United States Patent
DeRosa et al.

(10) Patent No.: US 10,975,369 B2
(45) Date of Patent: Apr. 13, 2021

(54) METHODS FOR PURIFICATION OF MESSENGER RNA

(71) Applicant: Translate Bio, Inc., Cambridge, MA (US)

(72) Inventors: Frank DeRosa, Cambridge, MA (US); Michael Heartlein, Cambridge, MA (US); Jonathan Abysalh, Cambridge, MA (US); Daniel Crawford, Cambridge, MA (US); Anusha Dias, Cambridge, MA (US); Shrirang Karve, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/907,086

(22) Filed: Feb. 27, 2018

(65) Prior Publication Data

US 2018/0251754 A1   Sep. 6, 2018

Related U.S. Application Data

(60) Provisional application No. 62/463,981, filed on Feb. 27, 2017.

(51) Int. Cl.
| | |
|---|---|
| C12Q 1/68 | (2018.01) |
| C07H 21/00 | (2006.01) |
| C12N 15/10 | (2006.01) |
| C07H 21/04 | (2006.01) |

(52) U.S. Cl.
CPC ......... *C12N 15/1003* (2013.01); *C07H 21/04* (2013.01); *C12N 15/1006* (2013.01); *C12N 15/1017* (2013.01); *C12N 15/1065* (2013.01); *C12N 2310/10* (2013.01); *C12Y 201/03003* (2013.01)

(58) Field of Classification Search
CPC .......................... C07H 21/00; C12N 15/1003; C12N 15/1006; C12N 15/1017
See application file for complete search history.

(56) References Cited

U.S. PATENT DOCUMENTS

| | | | | |
|---|---|---|---|---|
| 5,571,669 A * | 11/1996 | Lu | ........................ | C12Q 1/6865 435/6.12 |
| 6,180,778 B1 * | 1/2001 | Bastian | ............... | C12N 15/1006 536/25.3 |
| 9,308,281 B2 * | 4/2016 | Guild | ................... | A61K 31/713 |
| 9,850,269 B2 * | 12/2017 | DeRosa | .................. | C07H 21/02 |
| 10,155,785 B2 * | 12/2018 | Derosa | .................. | C07H 21/00 |
| 2002/0042080 A1 * | 4/2002 | Woods, Jr. | ............. | G01N 33/53 435/7.1 |
| 2002/0044919 A1 * | 4/2002 | Yu | ....................... | A61K 31/4164 424/85.1 |
| 2002/0151067 A1 * | 10/2002 | Garoff | .................. | C07K 14/005 435/456 |
| 2003/0083272 A1 * | 5/2003 | Wiederholt | ............... | A61P 3/00 514/44 R |
| 2003/0083274 A1 * | 5/2003 | Wright | ............... | C12N 15/1136 514/44 R |
| 2004/0009541 A1 * | 1/2004 | Singh | ..................... | C07H 21/04 435/7.23 |
| 2004/0039210 A1 * | 2/2004 | Cheng | .................. | C07D 233/84 548/311.1 |
| 2005/0048045 A1 * | 3/2005 | Shetty | .................... | A61K 38/45 424/94.5 |
| 2005/0181460 A1 * | 8/2005 | Ohno | ..................... | C07K 16/18 435/7.2 |
| 2006/0051834 A1 * | 3/2006 | Strey | ........................ | C07K 1/34 435/68.1 |
| 2007/0066552 A1 * | 3/2007 | Clarke | .................. | A61K 8/606 514/44 R |
| 2008/0248559 A1 * | 10/2008 | Inomata | ............ | C12N 15/1017 435/270 |
| 2010/0326827 A1 * | 12/2010 | Lin | .................. | G01N 27/44756 204/461 |
| 2012/0142756 A1 * | 6/2012 | Guild | .................. | C07K 14/505 514/44 A |
| 2014/0273058 A1 * | 9/2014 | Menon | .................. | G01N 1/405 435/29 |
| 2014/0343129 A1 * | 11/2014 | de Fougerolles | ...... | C12N 15/63 514/44 A |
| 2015/0119566 A1 * | 4/2015 | Li | ...................... | C12N 15/1006 536/25.42 |

(Continued)

FOREIGN PATENT DOCUMENTS

| | | |
|---|---|---|
| WO | WO2014/144767 A1 | 9/2014 |
| WO | WO-2015/164773 A1 | 10/2015 |
| WO | WO2016/193206 A1 | 12/2016 |

OTHER PUBLICATIONS kKiriko et al., Incorporation of Pseudouridine Into mRNA Yields Superior Nonimmunogenic Vector With Increased Translational Capacity and Biological Stability. Molecular Therapy 16 (11) : 1833 (Year: 2008).*
Moldow et al., Purification of Bacterial Membrane Proteins J. of Memb. Biology 10 : 137 (Year: 1972).*
Sahin et al., mRNA-based therapeutrics—developing a new class of drugs. Nature Reviews\Drug Discovery 13 : 759 (Year: 2014).*
Karikó, K. et al., "Generating the optimal mRNA for therapy: HPLC purification eliminates immune activation and improves translation of nucleoside-modified, protein-encoding mRNA", Nucleic Acids Research, GB, vol. 39, No. 21, Nov. 1, 2011, pp. e142-1.
Sahin, U. et al., "mRNA-based therapeutics—developing a new class of drugs", Nature Reviews Drug Discovery, vol. 13, No. 10, Sep. 19, 2014, pp. 759-780.

(Continued)

*Primary Examiner* — Ethan C Whisenant
(74) *Attorney, Agent, or Firm* — Proskauer Rose LLP; Fangli Chen; Julio J. Mendez

(57) ABSTRACT

The present invention relates, in part, to methods for large-scale purification of mRNA. The method includes, at least, a step of centrifuging an mRNA suspension in a centrifuge comprising a porous substrate at a speed sufficient to remove process contaminants and to precipitate purified mRNA composition onto the porous substrate.

16 Claims, 10 Drawing Sheets

(56) References Cited

U.S. PATENT DOCUMENTS

| | | | | |
|---|---|---|---|---|
| 2015/0376220 A1* | 12/2015 | DeRosa | ............... | C07H 21/02 |
| | | | | 536/23.1 |
| 2016/0038612 A1* | 2/2016 | Hoge | ................. | A61K 48/005 |
| | | | | 514/44 R |
| 2017/0056526 A1* | 3/2017 | Dohmen | ............ | A61K 48/0041 |
| 2018/0002393 A1* | 1/2018 | Bancel | ............... | C07K 16/2887 |
| 2018/0085391 A1* | 3/2018 | Bouchon | ............. | A61K 48/005 |
| 2018/0201967 A1* | 7/2018 | Eber | ................... | C12Q 1/6865 |
| 2018/0256750 A1* | 9/2018 | Butora | ............... | C07F 9/65586 |
| 2019/0054112 A1* | 2/2019 | Gregoire | ............ | A61K 9/1271 |

OTHER PUBLICATIONS

Search Report and Written Opinion for International Patent Application No. PCT/US18/19978, dated Aug. 30, 2018 (16 pages).

* cited by examiner

Un-Treated

Treated

METHODS FOR PURIFICATION OF MESSENGER RNA

CROSS-REFERENCE TO RELATED APPLICATIONS

The present application claims benefit of U.S. Provisional Application No. 62/463,981, filed Feb. 27, 2017, which is hereby incorporated by reference in its entirety.

BACKGROUND OF THE INVENTION

Messenger RNA (mRNA) therapeutics are promising new therapeutic agents; for example, mRNA replacement therapeutics can be alternatives to traditional protein replacement therapies. In an mRNA replacement therapeutic, an intact mRNA encoding a specific protein sequence is delivered to a target cell and is translated into an intact protein by the cell's native translational machinery. mRNA for such therapeutics typically are synthesized using in vitro transcription systems with enzymes such as RNA polymerases transcribing mRNA from template plasmid DNA, along with or followed by addition of a 5'-cap and 3'-polyadenylation. The result of such reactions is a composition which includes full-length mRNA and various undesirable contaminants, e.g., proteins, salts, buffers, and non-RNA nucleic acids, which are typically omitted to provide a clean and homogeneous mRNA that is usable in an mRNA replacement therapeutic.

Traditionally, mRNA is purified from in vitro transcription reactions by either commercially-available silica-based column systems, such as the Qiagen RNeasy® kit, or by protein extraction into an organic mix (phenol:chloroform: isoamyl alcohol) and subsequent ethanol precipitation. These methods are limited in scale as they can provide maximally five to ten mg of clean and homogeneous mRNA; thus, they are inadequate for the needs of clinical and commercial uses of mRNA. Recent novel methods, such as tangential flow filtration (TFF), have been modified to purify precipitated mRNA from in vitro transcription reactions; this has greatly increased the scale of purification. Additional methods suitable for the large-scale purification of mRNA, however, can be useful for the clinical and commercial development of mRNA therapeutics.

Accordingly, a need exists for a method that produces clean and homogeneous mRNA compositions, e.g., that are usable in purifying mRNA to a level of purity and integrity that is acceptable for therapeutic uses. The method described here is further advantageous in that it addresses this need, including preparation of large-scale quantities, yet in a cost-effective manner.

SUMMARY OF THE INVENTION

The present invention provides highly efficient methods for largescale purification of high quality messenger RNA (mRNA) suitable for clinical use. In particular, the present invention provides methods of purifying mRNA based on filtering centrifuge, resulting in unprecedented large-scale production of mRNA with high purity and integrity. The present invention thus allows more cost-effective manufacturing of mRNA at a scale capable of meeting various clinical and commercial needs.

An aspect of the present invention is a method for preparing a purified mRNA composition. The method includes steps of providing a suspension comprising precipitated mRNA; and centrifuging the suspension in a centrifuge comprising a porous substrate (e.g., a removable porous substrate) such that the precipitated mRNA is captured on the porous substrate, thereby purifying contaminants from the mRNA.

In another aspect, the invention features a method for purifying at least about 10 grams mRNA, comprising steps of: providing a suspension comprising precipitated mRNA; and centrifuging the suspension in a centrifuge comprising a porous substrate such that the precipitated mRNA is captured on the porous substrate, thereby purifying contaminants from the mRNA; wherein the total purified mRNA is recovered in an amount that results in a yield of at least about 80%, 85%, 90%, 91%, 92%, 93%, 94%, or 95%; and/or the total purified mRNA is substantially free of prematurely aborted RNA sequences and/or enzyme reagents used in in vitro synthesis.

In another aspect, the invention features a method for purifying at least about 25 grams mRNA, comprising steps of: providing a suspension comprising precipitated mRNA; and centrifuging the suspension in a centrifuge comprising a porous substrate such that the precipitated mRNA is captured on the porous substrate, thereby purifying contaminants from the mRNA; wherein the total purified mRNA is recovered in an amount that results in a yield of at least about 80%, 85%, 90%, 91%, 92%, 93%, 94%, or 95%; and/or the total purified mRNA is substantially free of prematurely aborted RNA sequences and/or enzyme reagents used in in vitro synthesis.

In another aspect, the invention features a method for purifying at least about 50 grams mRNA, comprising steps of: providing a suspension comprising precipitated mRNA; and centrifuging the suspension in a centrifuge comprising a porous substrate such that the precipitated mRNA is captured on the porous substrate, thereby purifying contaminants from the mRNA; wherein the total purified mRNA is recovered in an amount that results in a yield of at least about 80%, 85%, 90%, 91%, 92%, 93%, 94%, or 95%; and/or the total purified mRNA is substantially free of prematurely aborted RNA sequences and/or enzyme reagents used in in vitro synthesis.

In another aspect, the invention features a method for purifying at least about 100 grams mRNA, comprising steps of: providing a suspension comprising precipitated mRNA; and centrifuging the suspension in a centrifuge comprising a porous substrate such that the precipitated mRNA is captured on the porous substrate, thereby purifying contaminants from the mRNA; wherein the total purified mRNA is recovered in an amount that results in a yield of at least about 80%, 85%, 90%, 91%, 92%, 93%, 94%, or 95%; and/or the total purified mRNA is substantially free of prematurely aborted RNA sequences and/or enzyme reagents used in in vitro synthesis.

In another aspect, the invention features a method for purifying at least about 1 kilogram mRNA, comprising steps of: providing a suspension comprising precipitated mRNA; and centrifuging the suspension in a centrifuge comprising a porous substrate such that the precipitated mRNA is captured on the porous substrate, thereby purifying contaminants from the mRNA; wherein the total purified mRNA is recovered in an amount that results in a yield of at least about 80%, 85%, 90%, 91%, 92%, 93%, 94%, or 95%; and/or the total purified mRNA is substantially free of prematurely aborted RNA sequences and/or enzyme reagents used in in vitro synthesis.

In some embodiments, a porous substrate is removable. In embodiments, a porous substrate is a filter paper or a filter cloth.

In some embodiments, the method comprises a step of first producing the suspension of precipitated mRNA by providing a solution comprising mRNA and adding to the solution one or more agents that promote precipitation of mRNA.

In some embodiments, a suspension comprising precipitated mRNA comprises at least one filtration aid that is a dispersant. In some embodiments, a dispersant is one or more of ash, clay, diatomaceous earth, filtering agent, glass beads, plastic beads, polymers, polymer beads, polypropylene beads, polystyrene beads, salts (e.g., cellulose salts), sand, and sugars. In embodiments, a dispersant comprises powdered cellulose fiber.

In some embodiments, a suspension comprises at least 1 g, 10 g, 100 g, 1 kg, 10 kg, 100 kg, one metric ton (1000 kg), or ten metric tons (10,000 kg) of precipitated mRNA or any amount there between.

In some embodiments, the speed of the centrifuging of the mRNA suspension is between about 2000 RPM and about 4000 RPM, about 1000 RPM and about 5000 RPM, about 2000 RPM and about 4000 RPM, about 2000 RPM and about 3000 RPM, or about 2500 RPM and about 3500 RPM. In some embodiments, the speed is about 3000 RPM. In some embodiments, the speed is about 2500 RPM.

In some embodiments, a one or more agents that promote precipitation of mRNA are one or more of an alcohol, a buffer, a salt, and/or a surfactant.

In some embodiments, an alcohol is ethanol.

In some embodiments, a method further comprises adding one or more agents to the suspension that denature proteins and/or keep proteins soluble in an aqueous medium.

In some embodiments, a one or more agents that denature proteins and/or keep proteins soluble in an aqueous medium comprise a salt. In some embodiments, a salt is a chaotropic salt.

In some embodiments, a method further comprises a step of washing the purified mRNA composition with a solvent. In some embodiments, a solvent is an alcohol. In some embodiments, an alcohol is ethanol.

In some embodiments, a washing occurs via centrifugation. In some embodiments, centrifugation for washing the purified mRNA composition is at a speed of between about 50 RPM and about 500 RPM. In some embodiments, a speed is about 200 RPM. In embodiments, a speed is a speed between about 100 RPM to about 3000 RPM.

In some embodiments, a method further comprises a step of drying the captured mRNA. In some embodiments, drying occurs via centrifugation. In some embodiments, centrifugation for drying the captured mRNA is at a speed of between about 50 RPM and about 500 RPM, about 50 RPM and about 300 RPM, about 100 RPM and about 300 RPM, or about 150 RPM and about 250 RPM. In some embodiments, a speed is about 200 RPM. In embodiments, a speed is a speed between about 1000 RPM to about 3000 RPM.

In embodiments, dried purified mRNA is collected and stored at a temperature of or below about 0° C. for a time period of at least about one week to about two years. In embodiments, dried purified mRNA is stored at a temperature of or about 0° C. to about −40° C. or about 0° C., −10° C., −20° C., −30° C., or −40° C. In embodiments, dried purified mRNA is collected and stored for a time period of about one week to about two years, a time period of about one week to about one year, or a time period that is no more than about one year. In embodiments, dried purified mRNA is stored as a solid. In embodiments, dried purified mRNA is reconstituted following storage. In embodiments, dried purified mRNA has substantially the same integrity as prior to storage.

In some embodiments, a method further comprises a step of collecting the captured mRNA from the porous substrate. In some embodiments, collecting occurs while the centrifuge is centrifuging. In some embodiments, collecting occurs via a blade that removes a portion of the captured mRNA from the porous substrate. In some embodiments, collecting occurs while the centrifuge is not centrifuging.

In some embodiments, a method further comprises a step of solubilizing the purified mRNA in an aqueous medium, thereby obtaining a solution comprising purified mRNA. In some embodiments, an aqueous medium is water. In some embodiments, solubilizing occurs within the centrifuge. In some embodiments, solubilizing occurs outside the centrifuge.

In some embodiments, a method further comprises one or more steps for separating the dispersant from the purified mRNA composition. In some embodiments, a one or more steps for separating the dispersant from the purified mRNA comprise washing and drying the purified mRNA.

In some embodiments, a method further comprises solubilizing and eluting the purified mRNA using an aqueous medium while filtering the dispersant. In embodiments, an aqueous medium is water.

In some embodiments, a centrifuge is a continuous centrifuge and/or the centrifuge is orientated vertically or horizontally or the centrifuge is an inverted horizontal centrifuge.

In some embodiments, a centrifuge comprises a sample feed port and/or a sample discharge port.

In some embodiments, a centrifuge comprises a means for maintaining the porous substrate (e.g., a removable porous substrate) at a pre-selected temperature.

In some embodiments, a component external to the centrifuge comprises a means for maintaining the porous substrate (e.g., a removable porous substrate) at a pre-selected temperature.

In some embodiments, a one or more agents that promote precipitation of mRNA are a chaotropic salt and an alcohol. In some embodiments, a chaotropic salt is guanidine thiocyanate, and the alcohol is ethanol.

In some embodiments, mRNA is contacted with equal volumes of a first liquid that is a GSCN buffer and a second liquid that is absolute ethanol or aqueous ethanol.

In some embodiments, mRNA is contacted with a solution that comprises both the chaotropic salt and the alcohol.

In some embodiments, an mRNA suspension is loaded into the centrifuge at a rate of about 0.1 liter/min to about 5 liter/min or of about 0.1 liter/min to about 1 liter/min.

In some embodiments, recovery of purified mRNA is at least about 90%, 91%, 92%, 93%, 94%, 95%, 96%, or 97%.

In some embodiments, recovery of purified mRNA is at least 10 g, 20 g, 50 g, 100 g, 1 kg, 5 kg, 10 kg, 50 kg, or 100 kg per single batch.

In some embodiments, purified mRNA is substantially free of impurities from an mRNA synthesis process.

In some embodiments, purified mRNA is substantially free of prematurely aborted RNA sequences, DNA templates, and/or enzyme reagents used in in vitro synthesis of the single mRNA species.

In some embodiments, the mRNA is in vitro synthesized and the provided suspension comprises an in vitro mRNA synthesis reaction mixture.

In some embodiments, a provided suspension comprises prematurely aborted RNA sequences and/or enzyme reagents used in in vitro synthesis.

In some embodiments, a purified mRNA solution contains less than 5% of prematurely aborted RNA sequences and/or enzyme reagents used in in vitro synthesis. In some embodiments, a purified mRNA solution contains less than 1% of prematurely aborted RNA sequences and/or enzyme reagents used in in vitro synthesis. In some embodiments, a purified mRNA solution contains less than 0.5% of prematurely aborted RNA sequences and/or enzyme reagents used in in vitro synthesis. In some embodiments, a purified mRNA solution contains less than 0.1% of prematurely aborted RNA sequences and/or enzyme reagents used in in vitro synthesis. In some embodiments, the purified mRNA solution is substantially free of prematurely aborted RNA sequences and/or enzyme reagents used in in vitro synthesis.

In some embodiments, prematurely aborted RNA sequences and/or enzyme reagents used in in vitro synthesis are measured via silver stain, gel electrophoresis, HPLC, UPLC, and/or capillary electrophoresis. In some embodiments, prematurely aborted RNA sequences comprise less than 15 bases. In some embodiments, prematurely aborted RNA sequences comprise about 8-12 bases.

In some embodiments, enzyme reagents used in in vitro synthesis comprise T7 RNA polymerase, DNAse I, pyrophosphatase, and/or RNAse inhibitor.

In some embodiments, a composition comprising mRNA purified according to any centrifugation method described herein comprises a further purification (e.g., a solution comprising purified mRNA is further purified by a method such as dialysis, diafiltration, and/or ultrafiltration (e.g., tangential flow filtration (TFF)). In embodiments, a composition that is further purified (e.g., with dialysis, diafiltration, and/or ultrafiltration) is further purified using any centrifugation method described herein and is optionally then further purified by a method such as dialysis, diafiltration, and/or ultrafiltration (e.g., tangential flow filtration (TFF)). In embodiments, a purification method comprises at least two repeats of a method comprising centrifugation purification followed by purification via dialysis (e.g., tangential flow filtration (TFF)); for example, at least two, three, four, five, six, seven, eight, nine, or ten repeats. In embodiments, a purification method comprises two, three, four, five, six, seven, eight, nine, or ten repeats of a method comprising centrifugation purification followed by purification via dialysis, ultrafiltration, and/or diafiltration (e.g., tangential flow filtration (TFF)). In embodiments, a purification method comprises two, three, or four repeats of a method comprising centrifugation purification followed by purification via dialysis, ultrafiltration, and/or diafiltration (e.g., tangential flow filtration (TFF)).

In some embodiments, mRNA is purified before a cap and tail are added to the mRNA.

In some embodiments, mRNA is purified after a cap and tail are added to the mRNA.

In some embodiments, mRNA is purified after a cap is added.

In some embodiments, the mRNA is purified both before and after a cap and/or tail are added to the mRNA.

In some embodiments, mRNA is or greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, 15 kb, or 20 kb in length.

In some embodiments, mRNA comprises one or more nucleotide modifications. In some embodiments, a one or more modifications comprises modified sugars, modified bases, and/or modified sugar phosphate backbones.

In some embodiments, mRNA is unmodified.

In some embodiments, purified mRNA has an integrity of at least 80%, 85%, 90%, 92%, 94%, 95%, 96%, 97%, 98%, or 99%. In some embodiments, purified mRNA has an integrity of or greater than 95%. In some embodiments, purified mRNA has an integrity of or greater than 98%. In some embodiments, purified mRNA has an integrity of or greater than 99%.

In some embodiments, a centrifuge is a vertical centrifuge.

In some embodiments, a centrifuge is a horizontal centrifuge.

In some embodiments, a centrifuge is an inverted centrifuge.

In some embodiments, a method further comprises a step of dialyzing, ultrafiltering, and/or diafiltering the purified mRNA solution. In some embodiments, a method further comprises a purified mRNA solution is further purified using tangential flow filtration (TFF).

In another aspect, the invention features a composition comprising dried purified mRNA, wherein said mRNA is obtained by a method comprising: providing a suspension comprising precipitated mRNA; centrifuging the suspension in a centrifuge comprising a porous substrate such that the precipitated mRNA is captured on the porous substrate, thereby purifying contaminants from the mRNA; washing the purified mRNA composition with a solvent; and drying the captured mRNA.

In some embodiments, a washing step is followed by solubilizing and eluting purified mRNA using an aqueous medium.

In some embodiments, a solubilizing step is followed by purifying solubilized mRNA using dialysis, ultrafiltration, and/or diafiltration. In embodiments, a solubilizing step is followed by purifying solubilized mRNA using tangential flow filtration (TFF). In embodiments comprising a further filtration of a solubilized mRNA, an average filter pore size can be smaller than the filter pore size used in a centrifugation purification method as described herein. For example, an exemplary pore size can be about 0.01 micron to about 0.1 micron. In embodiments, further purification comprises use of a filter characterized by a molecular weight cutoff of about 1000 Da to about 300 kDa or about 1000 Da to about 1000 kDa. In embodiments, further purification comprises further purification comprises use of a filter characterized by a MWCO of about 1K, 3K, 5K, 10K, 30K, 50K, 100K, 300K, or 1000K such as a filter characterized by a MWCO of about 30K, 50K, 100K, or 300K.

In some embodiments, dried purified mRNA is stored at a temperature of about 0° C. to about −40° C. for a period of at least about a week to about two years, a period of up to about two years, or a period of up to about one year.

In some embodiments, dried purified mRNA is reconstituted following storage.

In some embodiments, dried purified mRNA has substantially the same integrity as prior to storage.

In some embodiments, mRNA is in vitro transcribed mRNA.

In some embodiments, mRNA is cap and tail (C/T) mRNA.

In some embodiments, mRNA is final mRNA.

In some embodiments, mRNA encodes cystic fibrosis transmembrane receptor (CFTR).

In some embodiments, mRNA encodes ornithine transcarbamylase (OTC).

Another aspect of the present invention is a purified mRNA composition prepared by an above-described aspect or embodiment. In some embodiments, the invention features a composition comprising purified mRNA (e.g., mRNA purified according to any method described herein. In some embodiments, a composition comprises at least one pharmaceutically-acceptable excipient (e.g., a pharmaceutical composition including the purified mRNA composition of the above aspect and at least one pharmaceutically-acceptable excipient).

In another aspect, the invention features a method for treating a disease or disorder comprising administering to a subject in need thereof any composition comprising purified mRNA as described herein. In some embodiments, a method for treating a disease or disorder including a step of administering to a subject in need thereof the pharmaceutical composition of the above aspect.

Another aspect of the present invention is a solution including purified mRNA prepared by an above-described aspect or embodiment.

Yet another aspect of the present invention is a pharmaceutical composition including the solution including purified mRNA of the above aspect and at least one pharmaceutically-acceptable excipient.

An aspect of the present invention is a method for treating a disease or disorder including a step of administering to a subject in need thereof the pharmaceutical composition of the above aspect.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the Drawings and the following detailed description and claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

Each of FIG. 9A

DEFINITIONS

Figure 1:
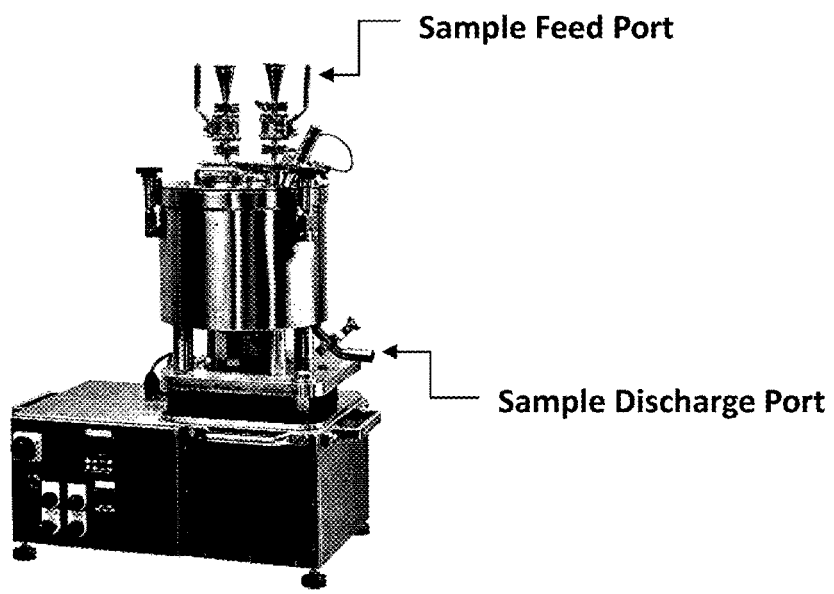
FIG. 1 is a photograph of a kilogram-scale laboratory filtering centrifuge with a six inch basket (428 $cm^2$).

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "batch" would not mean mRNA synthesized at different times that are combined to achieve the desired amount.

As used herein, the term "contaminants" as in "process contaminants" refers to substances inside a confined amount of liquid, gas, or solid, which differ from the chemical composition of the target material or compound. Contaminants are also referred to as impurities. Examples of contaminants or impurities include buffers, proteins (e.g., enzymes), nucleic acids, salts, solvents, and/or wash solutions.

As used herein, the term "dispersant" refers to a solid particulate which reduces the likelihood that an mRNA precipitate will form a hydrogel. A "dispersant" can be anything which is insoluble in a crash/wash buffer/solvent system wand which can mix evenly with the mRNA precipitate. Such dispersants could be any solid which is insoluble after saturation (at a given concentration). Examples of dispersants include and are not limited to one or more of ash, clay, diatomaceous earth, filtering agent, glass beads, plastic beads, polymers, polypropylene beads, polystyrene beads, salts (e.g., cellulose salts), sand, and sugars. The present invention can be used with or without a "dispersant". In embodiments, a dispersant is polymer microspheres (e.g., poly(styrene-co-divinylbenezene) microspheres).

As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end formation); (3) translation of an mRNA into a polypeptide or protein; and/or (4) post-translational modification of a polypeptide or protein. In this application, the terms "expression" and "production," and grammatical equivalent, are used inter-changeably.

As used herein, "full-length mRNA" is as characterized when using a specific assay, e.g., gel electrophoresis and detection using UV and UV absorption spectroscopy with separation by capillary electrophoresis. The length of an mRNA molecule that encodes a full-length polypeptide is at least 50% of the length of a full-length mRNA molecule that is transcribed from the target DNA and as obtained following any of the purification methods described herein, e.g., at least 60%, 70%, 80%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the length of a full-length mRNA molecule that is transcribed from the target DNA and prior to purification according to any method described herein.

As used herein, a "functional" biological molecule is a biological molecule in a form in which it exhibits a property and/or activity by which it is characterized.

As used herein, the term "hydrogel" refers to a network of hydrophilic polymer chains, e.g., mRNA, that forms a colloidal gel in which water is the dispersion medium. Using mRNA as an example, it is more difficult to extract or purify mRNA from a hydrogel than from a dry cake.

As used herein, the term "impurities" refers to substances inside a confined amount of liquid, gas, or solid, which differ from the chemical composition of the target material or compound. Impurities are also referred to as contaminants.

As used herein, the term "in vitro" refers to events that occur in an artificial environment, e.g., in a test tube or reaction vessel, in cell culture, etc., rather than within a multi-cellular organism.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man.

As used herein, the term "messenger RNA (mRNA)" refers to a polyribonucleotide that encodes at least one polypeptide. mRNA as used herein encompasses both modified and unmodified mRNA. mRNA may contain one or more coding and non-coding regions. mRNA can be purified from natural sources, produced using recombinant expression systems and optionally purified, in vitro transcribed, or chemically synthesized.

mRNA is typically thought of as the type of mRNA that carries information from DNA to the ribosome. The existence of mRNA is usually very brief and includes processing and translation, followed by degradation. Typically, mRNA includes a nucleotide sequence having a coding region that codes for a polypeptide, a 5' untranslated region (5' UTR) upstream of the coding region, a 3'untranslated region (3' UTR) downstream of the coding region, a cap at the 5' terminus and a polyA or polyadenylation region downstream of the 3'UTR. Typically, in eukaryotic organisms, mRNA processing comprises transcription of mRNA from DNA and the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

In some embodiments, an mRNA of the present invention lacks one or both of a cap and/or a tail. Thus, an mRNA may have a cap and lack a tail, an mRNA may have a tail and lack a cap, and an mRNA may lack a cap and lack a tail.

Any mRNA capable of being translated into one or more peptides (e.g., proteins) or peptide fragments is contemplated as within the scope of the present invention. In some embodiments; an mRNA encodes one or more naturally occurring peptides. In some embodiments, an mRNA encodes one or more modified or non-natural peptides.

As used herein, the term "mRNA integrity" generally refers to the quality of mRNA. In some embodiments, mRNA integrity refers to the percentage of mRNA that is not degraded (e.g., the percentage of full length mRNA) after a purification process such as any method described herein. mRNA integrity may be determined using methods well known in the art, for example, by RNA agarose gel electrophoresis (e.g., Ausubel et al., John Wiley & Sons, Inc., 1997, Current Protocols in Molecular Biology).

As used herein, the term "pharmaceutically acceptable", refers to substances that, within the scope of sound medical judgment, are suitable for use in contact with the tissues of human beings and animals without excessive toxicity, irritation, allergic response, or other problem or complication, commensurate with a reasonable benefit/risk ratio.

A "pharmaceutically acceptable excipient" means an excipient that is suitable for preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate.

Pharmaceutically acceptable salts are well known in the art. For example, S. M. Berge et al describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

The term "prematurely aborted RNA sequences", as used herein, refers to incomplete products of an mRNA synthesis reaction (e.g., an in vitro synthesis reaction). For a variety of reasons, RNA polymerases do not always complete transcription of a DNA template; i.e., RNA synthesis terminates prematurely. Possible causes of premature termination of RNA synthesis include quality of the DNA template, polymerase terminator sequences for a particular polymerase present in the template, degraded buffers, temperature, depletion of ribonucleotides, and mRNA secondary structures. Prematurely aborted RNA sequences may be any length that is less than the intended length of the desired transcriptional product. For example, prematurely aborted mRNA sequences may be less than 1000 bases, less than 500 bases, less than 100 bases, less than 50 bases, less than 40 bases, less than 30 bases, less than 20 bases, less than 15 bases, less than 10 bases or fewer.

As used herein, the term "porous substrate" is any solid substance that permits passage of fluid while preventing passage of at least a portion of a precipitate. In embodiments, a porous substrate is a removable porous substrate.

The porous substrate is not limited. The substrate may be cloth, glass, metal, paper, or a polymer. The pore size may be defined, e.g., of a specific micrometer or millimeter is size, or the pore size may be undefined. The substrate is "removable" from a centrifuge. Thus, the substrate may be part of a centrifuge drum (when the drum is removable from the remainder of the centrifuge). In some embodiments, the removable substrate lines (e.g., abuts) the interior surface of a centrifuge drum. In some embodiments, the substrate lines (e.g., abuts) the interior surface of a centrifuge drum having perforations which allow passage of fluid.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.2%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ng, 1 ng, 500 pg, 100 pg, 50 pg, 10 pg, or less.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION OF THE INVENTION

Methods of Purification mRNA can present challenges in both synthesis and in purification, particularly in large-scale preparations. The present invention relates to methods using a filtering centrifuge platform in conjunction with alternate precipitation and processing methods to successfully, capture, wash, and collect mRNA manufactured at a scale capable of meeting most clinical and commercial needs.

This novel disclosure illustrates a path forward for mRNA replacement therapeutics, allowing it to become a viable and successful alternative to the more traditional enzyme replacement therapies and biotherapeutics that are currently available.

To become a viable and successful alternative, the method for mRNA purification needs to be robust and scalable to ensure large-scale manufacturing capabilities are in place to meet all clinical and commercial needs. An appropriate mRNA purification method includes easy scalability while providing an equivalent or better product when compared to currently-available industry-standard mRNA purification methods. In particular, key attributes of the method should include high post purification mRNA yields, maintaining post purification mRNA integrity, and removal of process related contaminants (e.g., process enzymes) to below acceptable levels of contamination.

Here is disclosed use of a filtering centrifuge (e.g., vertical, horizontal, or inverted), as a platform for the purification of mRNA at clinical and commercial scales. Data presented here shows that the method is capable of capturing salt-EtOH precipitated mRNA solid via filtration through a centrifuge-associated porous solid substrate; the method simultaneously removes process contaminates and precipitated salts before harvest of a purified mRNA solid or suspension of purified mRNA in an aqueous medium.

The experimental results presented here include multiple scales (from one gram to one-hundred grams of mRNA) which verify the method's feasibility. Moreover, they show that the present invention is a capable (and at a lower cost) alternative to currently-available methods for purifying mRNA for experimental, clinical, or commercial use. Moreover, the present invention has a significant added benefit of scalability which is unavailable with the industry-standard methods and kits. The herein-disclosed methods will provide scalability beyond one-hundred gram single batches, including kilogram and metric ton batches. Finally, the herein-disclosed methods are extremely cost-effective relative to current processes such as chromatography or hollow fiber membrane-based purifications. See, e.g., WO 2011/068810; WO 2012/075040; WO 2014/152659; WO 2014/152673; WO 2014/152966; WO 2015/164773; WO 2016/004318; U.S. 62/420,413; and PCT/US16/57044.

Thus, methods described herein can be advantageous for the purification of mRNA, including large-scale quantities of mRNA (e.g., any batch size or loading volume described herein). For example, the purification methods as described herein can provide an increased percentage of full-length mRNA that is recovered from the purification relative to the amount of full-length mRNA prior to the purification, e.g., as compared to conventional purification methods. The purification methods as described herein can provide an increased percentage of full-length mRNA relative to the mixture of full-length mRNA and contaminants, e.g., as compared to conventional purification methods. The purification methods as described herein can provide mRNA having a high level of integrity acceptable for therapeutic, with minimal loss of full-length mRNA on account of the purification, e.g., as compared to conventional purification methods. Additionally, purified mRNA (including compositions or batches thereof) prepared according to methods described herein can have beneficial features. For example, a composition or batch of mRNA purified as described herein can: comprise an increased percentage of full-length mRNA molecules; comprise an increased quantity of full-length mRNA; and/or provide an increased activity (e.g., improved or increased protein expression). Such features can be beneficial for therapeutic uses. Accordingly, the present invention can be superior to currently-used methods for producing purified mRNA compositions, e.g., for use in mRNA replacement therapeutics. An aspect of the present invention is a method for preparing a purified mRNA composition.

The method includes steps of providing a suspension comprising precipitated mRNA; and centrifuging the suspension in a centrifuge comprising a porous substrate (e.g., a removable porous substrate) such that the precipitated mRNA is captured on the porous substrate, thereby purifying contaminants from the mRNA.

Precipitation of mRNA

Methods described herein are suitable for the purification of mRNA in a provided suspension comprising precipitated mRNA (e.g., an in vitro synthesis reaction mixture), wherein the mRNA can be precipitated using various precipitation methods known in the art. As used herein, the term "precipitation" (or any grammatical equivalent thereof) refers to the formation of a solid in a solution. When used in connection with mRNA, the term "precipitation" refers to the formation of insoluble or solid form of mRNA in a liquid.

Any and all methods suitable for precipitating mRNA may be used to practice the present invention.

In some embodiments, a one or more agents that promote precipitation of mRNA is a denaturing agent or results from denaturing conditions. As used herein, the term "denaturing condition" refers to any chemical or physical conditions that can cause denaturation. Exemplary denaturing conditions include, but are not limited to, use of chemical reagents, high temperatures, extreme pH, etc. In some embodiments, a denaturing condition is achieved through adding one or more denaturing agents to an impure preparation containing mRNA to be purified. In some embodiments, a denaturing agent suitable for the present invention is a protein and/or DNA denaturing agent. In some embodiments, a denaturing agent may be: 1) an enzyme (such as a serine proteinase or a DNase), 2) an acid, 3) a solvent, 4) a cross-linking agent, 5) a chaotropic agent, 6) a reducing agent, and/or 7) high ionic strength via high salt concentrations. In some embodiments, a particular agent may fall into more than one of these categories.

In some embodiments, one or more enzymes may be used as denaturing agents to degrade proteins and DNA templates used in mRNA synthesis. In some embodiments, suitable enzymes include, but are not limited to, serine proteases such as chymotrypsin and chymotrypsin-like serine proteases, trypsin and trypsin-like serine proteases, elastase and elastase-like serine proteases, subtilisin and subtilisin-like serine proteases, and combinations thereof, deoxyribonucleases (DNases) such as deoxyribonuclease I, II and/or IV, restriction enzymes such as EcoRI, EcoRII, BamHI, HindIII, SpeI, SphI, StuI, XbaI, and combination thereof.

In some embodiments, an acid may be used as a denaturing agent. In some embodiments, a suitable acid may be acetic acid, formic acid, oxalic acid, citric acid, benzoic acid, chloroacetic acid, dichloroacetic acid, trichloroacetic acid, ascorbic acid, sulfosalicylic acid, and combinations thereof.

In some embodiments, a solvent may be used as a denaturing agent. In some embodiments, a solvent may be isopropyl alcohol, acetone, methyl ethyl ketone, methyl isobutyl ketone, ethanol, methanol, denatonium, and combinations thereof. In embodiments, a solvent is an alcohol solvent (e.g., methanol, ethanol, or isopropanol). In embodiments, a solvent is a ketone solvent (e.g., acetone, methyl ethyl ketone, or methyl isobutyl ketone)

In some embodiments, a chaotropic agent may be sued as a denaturing agent. Choatropic agents are substances which disrupt the structure of macromolecules such as proteins and nucleic acids by interfering with non-covalent forces such as hydrogen bonds and van der Waals forces. In some embodiments, a chaotropic agent may be urea, thiourea, guanidinium chloride, guanidinium thiocyanate, guanidinium isothiocyanate, lithium acetate, magnesium chloride, sodium dodecyl sulfate, lithium perchlorate and combination thereof.

In some embodiments, a reducing agent may be used as a denaturing agent. Reducing agents are compounds that donate an electron to another species, thus becoming oxidized itself. In some embodiments, a reducing agent may be lithium aluminum hydride, sodium amalgam, diborane, sodium borohydride, sulfites, diisobutylaluminum hydride, phosphites, carbon monoxide, 2-mercaptoethanol, dithiothreitol, or tris(2-carboxyethyl)phosphine, and combinations thereof.

In some embodiments, one or more of pH, heat, and/or heavy metals (such as lead, mercury or cadmium) may also be used as denaturing agents to provide a denaturating condition. Extremes of pH are known to cause a protein to denature. Although the backbone of a protein chain is neutral, the amino acid residues that comprise the protein often contain acidic and basic groups. These groups are usually charged and can form salt bridges with a group of opposite charge. Accordingly, extremes of pH can change the charges on these acidic and basic groups, disrupting salt bridges.

In some embodiments, less drastic changes in pH may also affect the activity and solubility of a protein. Like individual amino acids, proteins have an isoelectric point at which the number of negative charges equals the number of positive charges. This is frequently the point of minimum water solubility. At the isoelectric pH, there is no net charge on the molecule. Individual molecules have a tendency to approach one another, coagulate, and precipitate out of solution. At a pH above or below the isoelectric pH, the molecules have a net negative or positive charge, respectively. Thus when protein molecules approach each other, they have the same overall charge and repulse each other.

In some embodiments, heat may be used as a denaturing agent. Heat can supply kinetic energy to protein molecules, causing their atoms to vibrate more rapidly. In some embodiments, this will disrupt relatively weak forces such as hydrogen bonds and hydrophobic interactions. Heat is also used in sterilization to denature and hence destroy the enzymes in bacteria.

In some embodiments, salts of metal ions such as mercury (II), lead(II), and silver may be used as denaturing agents due to their ability to form strong bonds with disulfide groups and with the carboxylate ions of the acidic amino acids. Thus, they disrupt both disulfide bridges and salt linkages and cause the protein to precipitate out of solution as an insoluble metal-protein salt.

In some embodiments, high concentrations of salt (high salinity) may also be used as a denaturing agent. High concentrations of salts are known to cause both proteins and nucleic acids to precipitate from an aqueous solution. In some embodiments, a high concentration of salt may be between 1M and 10M, inclusive. In some embodiments, a high concentration of salt may be between 2M and 9M, inclusive. In some embodiments, a high concentration of salt may be between 2M and 8M, inclusive. In some embodiments, a high concentration of salt may be between 2M and 5M, inclusive. In some embodiments, a high concentration of salt may be greater than 1M concentration. In some embodiments, a high concentration of salt may be greater than 2M concentration. In some embodiments, a high concentration of salt may be greater than 3M concentration. In some embodiments, a high concentration of salt may be greater than 4M concentration. In some embodiments, a high concentration of salt may be greater than 5M concentration. In some embodiments, a high concentration of salt may be greater than 6M concentration. In some embodiments, a high concentration of salt may be greater than 7M concentration. In some embodiments, a high concentration of salt may be greater than 8M concentration. In some embodiments, a single salt is used as a denaturing agent. In some embodiments, more than one salt is used as a denaturing agent.

In some embodiments, a salt used as a denaturing agent may be a calcium salt, an iron salt, a magnesium salt, a potassium salt, a sodium salt, or a combination thereof. Exemplary specific salts suitable for use as denaturing agents in some embodiments include, but are not limited to, potassium chloride (KCl), sodium chloride (NaCl), lithium chloride (LiCl), calcium chloride (CaCl$_2$), potassium bromide (KBr), sodium bromide (NaBr), lithium bromide (LiBr). In some embodiments, the denaturing agent the impure preparation is subjected to is potassium chloride (KCl). In some embodiments, KCl is added such that the resulting KCl concentration is about 1M or greater. In some embodiments, KCl is added such that the resulting KCl concentration is about 2 M or greater, 3 M or greater, 4 M or greater, or 5 M or greater.

In one embodiment, a high concentration solution of salt (e.g., a chaotropic salt such as guanidine thiocyanate) is added to an initial mRNA-containing composition to denature and solubilize contaminating proteins followed by addition of an alcohol (e.g., ethanol) to selectively precipitate mRNA. After mRNA precipitation, the resulting slurry is continuously stirred within the filtering device while pressure is applied to the slurry to push mother liquid through the filter or vacuum is applied to pull the mother liquor through the filter. Later, the precipitate within the slurry is washed or diafiltered using a salt/alcohol mixture followed by a high alcohol wash to yield a precipitate that is free of contamination, e.g., protein, salt, buffer, and non-RNA nucleic acid. Subsequent dissolution of the precipitated mRNA by water yields purified mRNA composition. In some embodiments, a solid support, such as polystyrene beads of a known size, are added to increase the purification capacity within a given filtration volume.

In some embodiments, the one or more agents that promote precipitation of mRNA are one or more of an alcohol, a buffer, a salt, and/or a surfactant. In some embodiments, the alcohol is ethanol.

In some embodiments, the method further includes a step of adding one or more agents that denature proteins (e.g., RNA polymerase and DNase I, which is added after transcription to remove DNA templates) and/or keep proteins soluble in an aqueous medium. In some embodiments, the one or more agents that denature proteins and/or keep proteins soluble in an aqueous medium is a salt, e.g., a chaotropic salt.

In embodiments of the methods, a precipitating step comprises the use of a chaotropic salt (e.g., guanidine thiocyanate) and/or an alcohol solvent (e.g., absolute ethanol or an aqueous solution of alcohol such as an aqueous ethanol solution). In embodiments of the methods, a precipitating step comprises the use of a chaotropic salt (e.g., guanidine thiocyanate) and an alcohol solvent (e.g., absolute ethanol or an aqueous solution of alcohol such as an aqueous ethanol solution).

In embodiments, a one or more agents that promote precipitation of mRNA comprises guanidine thiocyanate (e.g., a solution comprising about 1-5M guanidine thiocyanate). In embodiments, an agent that promotes precipitation of mRNA is a GSCN buffer (e.g., an aqueous solution comprising 4M guanidine thiocyanate, 25 mM sodium citrate pH 6.5, 0.5% N-lauroylsarcosine sodium salt).

In embodiments, a one or more agents that promote precipitation of mRNA includes an alcohol solvent (e.g., ethanol such as absolute ethanol). In embodiments, a one or more agents that promote precipitation of mRNA is an aqueous solution of an alcohol (e.g., aqueous ethanol). In embodiments, a one or more agents that promote precipitation of mRNA is absolute ethanol.

In embodiments, two agents are used to promote precipitation of mRNA, wherein one agent comprises guanidine thiocyanate (e.g., an aqueous solution of guanidine thiocyanate such as a GSCN buffer) and a second agent comprises an alcohol solvent (e.g., ethanol). In embodiments, the two agents are used sequentially or simultaneously. In embodiments, the method includes use of a solution comprising guanidine thiocyanate (e.g., a GSCN buffer) and an alcohol (e.g., absolute ethanol or an aqueous solution of an alcohol such as aqueous ethanol).

Filtration Aids (Including Dispersants)

In some embodiments, a filtration aid is used in a method described herein (e.g., during centrifugation).

In some embodiments, a filtration aid is a dispersant. In some embodiments, the precipitated mRNA composition includes at least one dispersant, e.g., one or more of ash, clay, diatomaceous earth, filtering agent, glass beads, plastic beads, polymers, polypropylene beads, polystyrene beads, salts (e.g., cellulose salts), sand, and sugars. In some embodiments, the dispersant is a bead. In some embodiments, the precipitated mRNA composition does not comprise a dispersant.

In some embodiments, a step of adding one or more agents that promotes precipitation of mRNA is performed in the absence of any dispersants.

In some embodiments, a step of adding one or more agents that promotes precipitation of mRNA is performed in the presence of at least one dispersant.

In some embodiments, a dispersant is added to the slurry obtained following the addition of one or more agents that promotes precipitation of mRNA.

Thus, in embodiments, a purification method may further include one or more steps for separating the dispersant from the purified mRNA precipitate, e.g., washing and drying the cake. The method may further include a step of solubilizing and eluting the purified mRNA from the cake using an aqueous medium, e.g., water, while filtering the dispersant. In embodiments, a precipitating step and a drying step may be performed simultaneously.

In embodiments, a filtration aid is a salt such as cellulose. In embodiments, a cellulose filtration aid is powdered cellulose fiber (e.g., Solka-Floc® or Sigmacell Cellulose 20). In embodiments, a cellulose filtration aid is a powdered cellulose fiber such as Solka-Floc® 100 NF or Sigmacell Cellulose Type 20 (20 µm).

Scale and Recovered Amounts

A particular advantage provided by the present invention is the ability to purify mRNA, in particular, mRNA synthesized in vitro, at a large or commercial scale. For example, in vitro synthesized mRNA may be purified at a scale of or greater than about 1 gram, 10 gram, 50 gram, 100 gram, 200 gram, 300 gram, 400 gram, 500 gram, 600 gram, 700 gram, 800 gram, 900 gram, 1 kg, 5 kg, 10 kg, 50 kg, 100 kg, 1000 kg, or 10000 kg per batch. In embodiments, in vitro synthesized mRNA may be purified at a scale of or greater than about 1 kg.

In one particular embodiment, in vitro synthesized mRNA may be purified at a scale of 10 gram per batch. In one particular embodiment, in vitro synthesized mRNA may be purified at a scale of 20 gram per batch. In one particular embodiment, in vitro synthesized mRNA may be purified at a scale of 25 gram per batch. In one particular embodiment, in vitro synthesized mRNA may be purified at a scale of 50 gram per batch. In another particular embodiment, in vitro synthesized mRNA may be purified at a scale of 100 gram per batch. In yet another particular embodiment, in vitro synthesized mRNA may be purified at a scale of 1 kg per batch. In yet another particular embodiment, in vitro synthesized mRNA may be purified at a scale of 10 kg per batch. In yet another particular embodiment, in vitro synthesized mRNA may be purified at a scale of 100 kg per batch. In yet another particular embodiment, in vitro synthesized mRNA may be purified at a scale of 1,000 kg per batch. In yet another particular embodiment, in vitro synthesized mRNA may be purified at a scale of 10,000 kg per batch.

As shown in the examples below, a batch comprising purified mRNA in the amount of 10 grams or greater (e.g., 25 grams, 50 grams, or 100 grams, or more) can be achieved easily with the methods of the invention.

In some embodiments, the mRNA is purified at a scale of or greater than 1 gram, 5 gram, 10 gram, 15 gram, 20 gram, 25 gram, 30 gram, 35 gram, 40 gram, 45 gram, 50 gram, 75 gram, 100 gram, 150 gram, 200 gram, 250 gram, 300 gram, 350 gram, 400 gram, 450 gram, 500 gram, 550 gram, 600 gram, 650 gram, 700 gram, 750 gram, 800 gram, 850 gram, 900 gram, 950 gram, 1 kg, 2.5 kg, 5 kg, 7.5 kg, 10 kg, 25 kg, 50 kg, 75 kg, or 100 kg per batch.

In some embodiments, the solution comprising mRNA includes at least one gram, ten grams, one-hundred grams, one kilogram, ten kilograms, one-hundred kilograms, one metric ton, ten metric tons, or more mRNA, or any amount there between. In some embodiments, a method described herein is used to purify an amount of mRNA that is at least about 250 mg mRNA. In one embodiment, a method described herein is used to purify an amount of mRNA that is at least about 250 mg mRNA, about 500 mg mRNA, about 750 mg mRNA, about 1000 mg mRNA, about 1500 mg mRNA, about 2000 mg mRNA, or about 2500 mg mRNA. In embodiments, a method described herein is used to purify an amount of mRNA that is at least about 250 mg mRNA to about 500 g mRNA. In embodiments, a method described herein is used to purify an amount of mRNA that is at least about 500 mg mRNA to about 250 g mRNA, about 500 mg mRNA to about 100 g mRNA, about 500 mg mRNA to about 50 g mRNA, about 500 mg mRNA to about 25 g mRNA, about 500 mg mRNA to about 10 g mRNA, or about 500 mg mRNA to about 5 g mRNA. In embodiments, a method described herein is used to purify an amount of mRNA that is at least about 100 mg mRNA to about 10 g mRNA, about 100 mg mRNA to about 5 g mRNA, or about 100 mg mRNA to about 1 g mRNA.

In some embodiments, a method described herein provides a recovered amount of purified mRNA that is at least about 50%, about 55%, about 60%, about 65%, about 70%, about 75%, about 80%, about 85%, about 90%, or about 95%. In some embodiments, a method described herein provides a recovered amount of purified mRNA that is at least about 70% (e.g., at least about 70%, 75%, 80%, or 85%).

Centrifugation Speed

In some embodiments, the speed of the centrifuging of the mRNA suspension is between about 2000 RPM and about 4000 RPM, e.g., about 3000 RPM. In some embodiments, the speed is about 2500 RPM. These centrifugation speeds produce a finer mRNA precipitate than speeds outside the above-mentioned ranges.

Exemplary Optional Steps for Purification

Methods described herein can be readily modified by the person of ordinary skill in the art. Exemplary modifications, including additional exemplary steps, are described herein.

In some embodiments, the method further includes a step of washing, e.g., via centrifugation, the purified mRNA composition with an organic solvent, e.g., an alcohol. In some embodiments, the alcohol is ethanol. The centrifugation for washing the purified mRNA composition may be at a speed of between about 50 RPM and about 500 RPM, e.g., about 200 RPM. In embodiments, a speed is a speed between about 100 RPM to about 3000 RPM.

In some embodiments, the method further includes a step of drying, e.g., via centrifugation, the purified mRNA composition. The centrifugation for drying the purified mRNA composition may be at a speed of between about 50 RPM and about 500 RPM, e.g., about 200 RPM. In embodiments, a speed is a speed between about 1000 RPM to about 3000 RPM.

In some embodiments, the method further includes a step of collecting the purified mRNA composition from the porous substrate (e.g., a removable porous substrate). The collecting may occur while the centrifuge is centrifuging or while the centrifuge is not centrifuging. The collecting may occur via a blade that removes a portion (e.g., a ribbon and a block) of the purified mRNA composition that is precipitated onto the porous substrate (e.g., a removable porous substrate).

In some embodiments, the method further includes a step of solubilizing the purified mRNA composition in an aqueous medium, e.g., water, thereby obtaining a solution comprising purified mRNA. The solubilizing may occur within the centrifuge or outside the centrifuge. The solubilizing may include a step of pulverizing the purified mRNA composition.

In some embodiments, the method further includes one or more steps for separating the dispersant from the purified mRNA composition. The one or more steps for separating the dispersant from the purified mRNA precipitate may include washing and drying (e.g., multiple times) the purified mRNA composition. The separating may include pulverizing the purified mRNA composition. The separating the dispersant from the purified mRNA precipitant may further include solubilizing and eluting the purified mRNA from the purified mRNA composition using an aqueous medium, e.g., water, while filtering the dispersant.

In some embodiments, a method according to the present invention further comprises a step of further purifying (e.g., dialyzing, diafiltering, and/or ultrafiltering) the purified mRNA solution. In some embodiments, the purified mRNA solution is dialyzed with 1 mM sodium citrate using a 100 kDa molecular weight cut-off (MWCO) membrane.

A purification process according to the present invention may be carried out during or subsequent to synthesis. For example, mRNA may be purified as described herein before a cap and/or tail are added to the mRNA. In some embodiments, the mRNA is purified after a cap and/or tail are added to the mRNA. In some embodiments, the mRNA is purified after a cap is added. In some embodiments, the mRNA is purified both before and after a cap and/or tail are added to the mRNA. In general, a purification step as described herein may be performed after each step of mRNA synthesis, optionally along with other purification processes, such as dialysis, diafiltration, and/or ultrafiltration; e.g., using tangential flow filtration (TFF). For example, mRNA may undergo further purification (e.g., dialysis, diafiltration, and/or ultrafiltration) to remove shortmers after initial synthesis (e.g., with or without a tail) and then be subjected to precipitation and purification as described herein, then after addition of the cap and/or tail, be purified again by precipitation and purification. In embodiments, a further purification comprises use of tangential flow filtration (TFF).

Characterization of Purified mRNA

In various embodiments, the present invention may be used to purify mRNA in vitro synthesized from an impure preparation containing an in vitro mRNA synthesis reaction mixture. In some embodiments, the impure preparation comprises prematurely aborted RNA sequences and/or enzyme reagents used in in vitro synthesis.

In some embodiments, the purified mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention.

In some embodiments, the purified mRNA molecules are detected using UV absorption spectroscopy with separation by capillary electrophoresis. In this embodiment, a composition or a batch provides a lower number of peaks, peaks with a narrower base, and/or taller peaks when detected using capillary electrophoresis relative to a composition or a batch having a lower percentage of full-length mRNA molecules. For example, the composition or the batch provides a lower number of peaks, peaks with a narrower base, and/or taller peaks when detected using capillary electrophoresis relative to a composition or a batch including mRNA transcribed using T7 or SP6 as described herein.

In some embodiments, a method described herein provides purified mRNA that is substantially free of any enzymes or reagents in the solution used prepare the mRNA (e.g., T7 or S6 RNA polymerase, DNAse I, pyrophosphatase, and/or RNAse inhibitor). In some embodiments, a solution comprising mRNA to be purified comprises enzyme reagents used in in vitro synthesis, including RNA polymerases (e.g., T7 RNA polymerase ("T7") and/or SP6 RNA polymerase ("SP6")), DNAse I, pyrophosphatase, and/or RNAse inhibitor, or any combination thereof. In some embodiments, the method described herein provides purified mRNA that is substantially free of T7 RNA polymerase ("T7"). In some embodiments, the method described herein provides purified mRNA that is substantially free of SP6 RNA polymerase ("SP6"). In some embodiments, the method described herein provides purified mRNA that is substantially free of DNAse I. In some embodiments, the method described herein provides purified mRNA that is substantially free of pyrophosphatase. In some embodiments, the method described herein provides purified mRNA that is substantially free of RNAse inhibitor. In some embodiments, the determination of being substantially free of any of the aforementioned enzymes or reagents used prepare the mRNA is conducted by agarose gel electrophoresis. In some embodiments, the determination of being substantially free of any of the aforementioned enzymes or reagents used to prepare the mRNA is conducted by SDS-PAGE with silver staining.

In some embodiments, a method according to the invention removes more than about 90% of T7 RNA polymerase used in in vitro synthesis. In some embodiments, a method according to the invention removes more than about 95% of T7 RNA polymerase used in in vitro synthesis. In some embodiments, a method according to the invention removes more than about 98% of T7 RNA polymerase used in in vitro synthesis. In some embodiments, a method according to the invention removes more than about 99% of T7 RNA polymerase used in in vitro synthesis. In some embodiments, a method according to the invention removes substantially all T7 RNA polymerase used in in vitro synthesis. In some embodiments, mRNA purified according to the present invention contains less than about 5% (e.g., less than about 4%, 3%, 2%, or 1%) of T7 polymerase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of T7 polymerase used in in vitro synthesis. In some embodiments, mRNA purified according to the present invention contains undetectable T7 polymerase used in in vitro synthesis including as determined by, e.g., agarose gel electrophoresis with ethidium bromide and/or Coomassie staining. The percentages of T7 polymerase as described above can be determined by densitometry quantification of agarose gel electrophoresis. Alternatively, the percentages of T7 polymerase as described above can be determined by known techniques, such as by known chromatographic separation and quantification methods.

In some embodiments, a method according to the invention removes more than about 90% of SP6 RNA polymerase used in in vitro synthesis. In some embodiments, a method according to the invention removes more than about 95% of SP6 RNA polymerase used in in vitro synthesis. In some embodiments, a method according to the invention removes more than about 98% of SP6 RNA polymerase used in in vitro synthesis. In some embodiments, a method according to the invention removes more than about 99% of SP6 RNA polymerase used in in vitro synthesis. In some embodiments, a method according to the invention removes substantially all SP6 RNA polymerase used in in vitro synthesis. In some embodiments, mRNA purified according to the present invention contains less than about 5% (e.g., less than about 4%, 3%, 2%, or 1%) of SP6 polymerase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of SP6 polymerase used in in vitro synthesis. In some embodiments, mRNA purified according to the present invention contains undetectable SP6 polymerase used in in vitro synthesis including as determined by, e.g., agarose gel electrophoresis with ethidium bromide and/or Coomassie staining. The percentages of SP6 polymerase as described above can be determined by densitometry quantification of agarose gel electrophoresis. Alternatively, the percentages of SP6 polymerase as described above can be determined by known techniques, such as by known chromatographic separation and quantification methods.

In some embodiments, a method according to the invention removes more than about 90% of DNAse I used in in vitro synthesis. In some embodiments, a method according to the invention removes more than about 95% of DNAse I used in in vitro synthesis. In some embodiments, a method according to the invention removes more than about 98% of DNAse I used in in vitro synthesis. In some embodiments, a method according to the invention removes more than about 99% of DNAse I used in in vitro synthesis. In some embodiments, a method according to the invention removes substantially all DNAse I used in in vitro synthesis. In some embodiments, mRNA purified according to the present invention contains less than about 5% (e.g., less than about 4%, 3%, 2%, or 1%) of DNAse I used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of DNAse I used in in vitro synthesis. In some embodiments, mRNA purified according to the present invention contains undetectable DNAse I used in in vitro synthesis including as determined by, e.g., agarose gel electrophoresis with ethidium bromide and/or Coomassie staining. The percentages of DNAse I as described above can be determined by densitometry quantification of agarose gel electrophoresis. Alternatively, the percentages of DNAse I as described above can be determined by known techniques, such as by known chromatographic separation and quantification methods.

In some embodiments, a method according to the invention removes more than about 90% of pyrophosphatase used in in vitro synthesis. In some embodiments, a method according to the invention removes more than about 95% of pyrophosphatase used in in vitro synthesis. In some embodiments, a method according to the invention removes more than about 98% of pyrophosphatase used in in vitro synthesis. In some embodiments, a method according to the invention removes more than about 99% of pyrophosphatase used in in vitro synthesis. In some embodiments, a method according to the invention removes substantially all pyrophosphatase used in in vitro synthesis. In some embodiments, a method according to the invention removes substantially all pyrophosphatase used in in vitro synthesis. In some embodiments, mRNA purified according to the present invention contains less than about 5% (e.g., less than about 4%, 3%, 2%, or 1%) of pyrophosphatase used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of pyrophosphatase used in in vitro synthesis. In some embodiments, mRNA purified according to the present invention contains undetectable pyrophosphatase used in in vitro synthesis including as determined by, e.g., agarose gel electrophoresis with ethidium bromide and/or Coomassie staining. The percentages of pyrophosphatase as described above can be determined by densitometry quantification of agarose gel electrophoresis. Alternatively, the percentages of pyrophosphatase as described above can be determined by known techniques, such as by known chromatographic separation and quantification methods.

In some embodiments, a method according to the invention removes more than about 90% of RNAse inhibitor used in in vitro synthesis. In some embodiments, a method according to the invention removes more than about 95% of RNAse inhibitor used in in vitro synthesis. In some embodiments, a method according to the invention removes more than about 98% of RNAse inhibitor used in in vitro synthesis. In some embodiments, a method according to the invention removes more than about 99% of RNAse inhibitor used in in vitro synthesis. In some embodiments, a method according to the invention removes substantially all RNAse inhibitor used in in vitro synthesis. In some embodiments, mRNA purified according to the present invention contains less than about 5% (e.g., less than about 4%, 3%, 2%, or 1%) of RNAse inhibitor used in in vitro synthesis. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of RNAse inhibitor used in in vitro synthesis. In some embodiments, mRNA purified according to the present invention contains undetectable RNAse inhibitor used in in vitro synthesis including as determined by, e.g., agarose gel electrophoresis with ethidium bromide and/or Coomassie staining. The percentages of RNAse inhibitor as described above can be determined by densitometry quantification of agarose gel electrophoresis. Alternatively, the percentages of RNAse inhibitor as described above can be determined by known techniques, such as by known chromatographic separation and quantification methods.

In some embodiments, the present invention removes or eliminates a high degree of prematurely aborted RNA sequences (also known as "shortmers"). In some embodiments, a method according to the invention removes more than about 90%, 95%, 96%, 97%, 98%, 99% or substantially all prematurely aborted RNA sequences. In some embodiments, mRNA purified according to the present invention is substantially free of prematurely aborted RNA sequences. In some embodiments, mRNA purified according to the present invention contains less than about 5% (e.g., less than about 4%, 3%, 2%, or 1%) of prematurely aborted RNA sequences. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, mRNA purified according to the present invention contains undetectable prematurely aborted RNA sequences as determined by, e.g., ethidium bromide and/or Coomassie staining. In some embodiments, prematurely aborted RNA sequences comprise less than 15 bases (e.g., less than 14, 13, 12, 11, 10, 9, 8, 7, 6, 5, 4, or 3 bases). In some embodiments, the prematurely aborted RNA sequences contain about 8-15, 8-14, 8-13, 8-12, 8-11, or 8-10 bases.

In some embodiments, a purified mRNA solution contains less than about 5% (e.g., less than about 4.5%, 4%, 3.5%, 3%, 2.5%, 2%, 1.5%, 1%, 0.5%, 0.1%) of prematurely aborted RNA sequences and/or enzyme reagents used in in vitro synthesis. In certain embodiments, the purified mRNA solution contains less than about 1% (e.g., less than about 0.9%, 0.8%, 0.7%, 0.6%, or 0.5%) of prematurely aborted RNA sequences and/or enzyme reagents used in in vitro synthesis. In certain embodiments, a purified mRNA solution contains less than about 0.5% (e.g., less than about 0.4%, 0.3%, 0.2%, or 0.1%) of prematurely aborted RNA sequences and/or enzyme reagents used in in vitro synthesis. In some embodiments, a purified mRNA solution contains less than about 0.1% of prematurely aborted RNA sequences and/or enzyme reagents used in in vitro synthesis. In some embodiments, a purified mRNA solution is substantially free of prematurely aborted RNA sequences and/or enzyme reagents used in in vitro synthesis.

In some embodiments, prematurely aborted RNA sequences and/or enzyme reagents used in in vitro synthesis are measured via silver stain, gel electrophoresis, high-performance liquid chromatography (HPLC), ultra-performance liquid chromatography (UPLC), and/or capillary electrophoresis.

In some embodiments, the prematurely aborted RNA sequences contain less than 15 bases (e.g., less than 14, 13, 12, 11, 10, 9, 8, 7, 6, 5, 4, or 3 bases). In some embodiments, the prematurely aborted RNA sequences contain about 8-15, 8-14, 8-13, 8-12, 8-11, or 8-10 bases.

In some embodiments, mRNA purified using a method described herein maintain high degree of integrity. mRNA integrity may be determined using methods particularly described herein, such as TAE Agarose gel electrophoresis or by SDS-PAGE with silver staining, or by methods well known in the art, for example, by RNA agarose gel electrophoresis. In some embodiments, purified mRNA has an integrity of or greater than about 95% (e.g., of or greater than about 96%, 97%, 98%, or 99%). In some embodiments, the purified mRNA has an integrity of or greater than about 98%. In some embodiments, the purified mRNA has an integrity of or greater than about 99%. In some embodiments, mRNA purified according to the present invention has an integrity of approximately 100%. In some embodiments, a method described herein provides a composition having an increased activity, e.g., at least two-fold, three-fold, four-fold, five-fold, or more, of translated polypeptides relative to a composition having a lower percentage of full-length mRNA molecules.

mRNAs

The purification methods described herein are suitable for purification of any mRNA. Exemplary mRNAs are described herein.

The present invention may be used to purify any mRNA. mRNA is typically thought of as the type of RNA that carries information from DNA to the ribosome. The existence of mRNA is typically very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

The present invention may be used to purify mRNAs encoding a variety of proteins. Non-limiting examples of purification include purification of mRNAs encoding OTC and CFTR.

Synthesis, Including Large Scale-Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. The presence of these reagents is undesirable in the final product according to several embodiments and may thus be referred to as impurities and a preparation containing one or more of these impurities may be referred to as an impure preparation. In some embodiments, the in vitro transcribing occurs in a single batch.

Another aspect of the present invention is a method for producing a composition enriched for full-length mRNA molecules which are greater than 500 nucleotides in length. The method includes a step of transcribing in vitro one or more target DNA molecules with an RNA polymerase (e.g., SP6 or T7) to produce purified mRNA molecules in which at least 80% of the purified mRNA molecules are full-length mRNA molecules. The method produces a composition including at least 100 mg of mRNA that is enriched for full-length mRNA.

In another aspect of the present invention is a method for large-scale production of full-length mRNA molecules. The method includes a step of transcribing in vitro in a single batch one or more target DNA molecules with an RNA polymerase (e.g., SP6 or T7) to produce purified mRNA molecules that are greater than 500 nucleotides in length. At least 80% of the purified mRNA molecules are full-length mRNA molecules. The large-scale production produces at least 100 mg of mRNA in a single batch.

Yet another aspect of the present invention is a method for producing a composition enriched for full-length polypeptides. The method includes a step of transcribing in vitro in a single batch at least one target DNA molecule with an RNA polymerase (e.g., SP6 or T7) to produce at least 100 mg of mRNA molecules that are greater than 500 nucleotides in length; at least 80% of the mRNA molecules are full-length mRNA molecules. The method further includes a step of translating the mRNA molecules to produce a composition enriched for full-length polypeptides.

In some embodiments, at least 81%, 82%, 83%, 84%, 85%, 86%, 87%, 88%, 89%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the purified mRNA molecules are full-length mRNA molecules.

In some embodiments, a composition or a batch includes at least 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more mRNA.

In some embodiments, the mRNA molecules are greater than 600, 700, 800, 900, 1000, 2000, 3000, 4000, 5000, 10,000 or more nucleotides in length; also included in the present invention is mRNA having any length in between.

In some embodiments, a composition or a batch has a greater percentage of full-length mRNA molecules than a composition or a batch including mRNA transcribed using T7.

In some embodiments, a composition provides an increased quantity, e.g., at least two-fold, three-fold, four-fold, five-fold, or more, of full-length polypeptides relative to a composition having a lower percentage of full-length mRNA molecules.

In some embodiments, a composition provides an increased activity, e.g., at least two-fold, three-fold, four-fold, five-fold, or more, of translated polypeptides relative to a composition having a lower percentage of full-length mRNA molecules.

In some embodiments, a composition or a batch is prepared without a step of specifically removing mRNA molecules that are not full-length mRNA molecules.

In some embodiments, the SP6 comprises a tag which allows the SP6 to be purified, isolated, and/or detected. An exemplary tag is a his-tag. Other such tags known in the art are included in the present invention.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, mRNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which is described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these features improve the stability and/or pharmacokinetic properties (e.g., half-life) of the polynucleotide relative to the same polynucleotide without such features, and include, for example features made to improve such polynucleotides' resistance to in vivo nuclease digestion.

mRNA Length

According to various embodiments, the present invention may be used to purify in vitro synthesized mRNA of a variety of lengths. In some embodiments, the present invention may be used to purify in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to purify in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length. For example, typical mRNAs may be about 1 kb to about 5 kb in length. More typically, the mRNA will have a length of about 1 kb to about 3 kb. However, in some embodiments, the mRNA in the composition of the invention is much longer (greater than about 20 kb). In some embodiments, one or more modifications are selected from modified nucleotide, modified sugar phosphate backbones, 5' and/or 3' untranslated region. In some embodiments, the present invention may be used to purify in vitro synthesized mRNA that is unmodified.

Modified mRNA Nucleotides

In certain embodiments, mRNA nucleotides are modified to provide "modified mRNA." A modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

In some embodiments, a method further includes a step of adding a cap and/or adding a polyA tail to the purified mRNA or to the full-length mRNA. Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

While mRNA provided from in vitro transcription reactions may be desirable in some embodiments, other sources of mRNA are contemplated as within the scope of the invention including wild-type mRNA produced from bacteria, fungi, plants, and/or animals.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 10 and 50 nucleotides in length. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 10 and 50 nucleotides in length or longer. In some embodiments, a 3' untranslated region may be between 50 and 500 nucleotides in length or longer.

Centrifuges

Any centrifuge may be used in the present invention if it provides centrifugation and is capable of separating solids and liquid from a solid-liquid mixture by passing the liquid through a porous substrate (e.g., a basket, a filter, a perforated centrifuge drum, and a screen).

Non-limiting examples of suitable centrifuge types include batch filtering centrifuges, inverting filter centrifuges, pusher centrifuges, peeler centrifuges (e.g., horizontal peeler centrifuge, vertical peeler centrifuge, and siphon peeler centrifuge), pendulum centrifuges, screen/scroll centrifuges, and sliding discharge centrifuges. In some embodiments, the centrifuge is a continuous centrifuge and/or the centrifuge is orientated vertically or horizontally or the centrifuge is an inverted horizontal centrifuge.

In some embodiments, the centrifuge comprises a sample feed port and/or a sample discharge port.

In some embodiments, the centrifuge comprises a means for maintaining the porous substrate (e.g., a removable porous substrate) at a pre-selected temperature.

In some embodiments, a component external to the centrifuge comprises a means for maintaining the porous substrate (e.g., a removable porous substrate) at a pre-selected temperature.

In some embodiments the centrifuge is capable of reversibly attaching to a removable porous substrate.

Any filtration-type centrifuge may be used in the present invention. Often, such centrifuges include a drum which is perforated to allow fluid flow. The perforated drum accepts a porous substrate, e.g., a filter cloth, a filter paper, a screen, and a wire mesh. In embodiments, a porous substrate is a removable porous substrate A suspension flows from the inside to the outside through the porous substrate (e.g., a removable porous substrate) and then through the perforated drum. In this way the solid material is restrained and liquids are removed from the suspension.

A porous substrate (e.g., a removable porous substrate such as filter cloth or filter paper) used in any of the methods described herein may feature variety of filter pore sizes and types. For example, a centrifuge filter can have an average pore size of about 0.01 micron to about 200 microns, about 1 micron to about 2000 microns, about 0.2 microns to about 5 micron, or about one micron to about 3 microns. In embodiments, an average pore size is about 0.5 micron or greater, about 0.75 micron or greater, about 1 micron or greater, about 2 microns or greater, about 3 microns or greater, about 4 microns or greater, or about 5 microns or greater. Methods herein can accommodate a variety of filter pore sizes while still retaining mRNA and without fouling a filter.

In each of these centrifuges, the drum may be orientated vertically or orientated horizontally.

Suitable centrifuges may be batch fed or continuously fed.

Centrifuges suitable in the present invention are well-known in the art. See, e.g., Scott, K. and Hughes, R., "Industrial Membrane Separation Technology". Springer Science & Business Media, 1996; Tarleton, S. and Wakeman, R., "Filtration: Equipment Selection, Modelling and Process Simulation", Elsevier, 1999; Tarleton, S. and Wakeman, R., "Solid/Liquid Separation: Scale-up of Industrial Equipment". Elsevier, 2005; Wakeman, R. and Tarleton, S., "Solid/Liquid Separation: Principles of Industrial Filtration". Elsevier, 2005; Tarleton, S. and Wakeman, R., "Solid/liquid separation: equipment selection and process design". Elsevier, 2006; and Sutherland, K. and Chase, G., "Filters and Filtration Handbook". Elsevier, 2011, each of which is incorporated herein by reference in their entireties. Also, see U.S. Pat. Nos. 1,292,758A; 1,478,660A; 3,269,028A; 3,411,631A; 3,419,148A; 3,438,500A; 3,483,991A; 3,491,888A; 3,623,613A; 3,684,099A; 3,774,769A; 3,980,563A; 4,193,874A; 4,193,874A; 4,193,874A; 4,269,711A; 4,381,236A; 4,944,874A; 5,004,540A; 5,091,084A; 5,092,995A; 5,244,567A; 5,277,804A; 5,286,378A; 5,306,423A; 5,378,364A; 5,380,434A; 5,397,471A; 5,421,997A; 5,433,849A; 5,468,389A; 5,472,602A; 5,713,826A; 6,736,968B2; 6,736,968B2; 6,736,968B2; 7,168,571B2; 7,425,264B2; 8,021,289B2; 8,257,587B2; 9,126,233B2; 9,297,581B2; US20040108281A1; US20040108281A1; US20050245381A1; US20060021931A1; US20060175245A1; US20080149558A1; US20100120598A1; US20100216623A1; US20120285868A1; US20140360039A1; AU2007350788A1; AU2007350788B2; EP1372862A1; EP3040127A1; EP845296A1; WO2004033105A1; WO2008122067A1; WO2014043541A1; WO2016025862A1; WO2016112426A1; WO2016112427A1; and WO2016112428A1, each of which is incorporated herein by reference in their entireties.

A centrifuge described above may be used in the below-described methods and to produce the below-described compositions.

Compositions and Methods of Treatment

The present invention provides methods for producing a composition enriched with full-length mRNA molecules which are greater than 500 nucleotides in length and encoding for a peptide or polypeptide of interest. The present invention also provides methods for producing a therapeutic composition enriched with full-length mRNA molecules encoding a peptide or polypeptide of interest for use in the delivery to or treatment of a subject, e.g., a human subject or a cell of a human subject or a cell that is treated and delivered to a human subject.

Accordingly, in certain embodiments the present invention provides a method for producing a therapeutic composition enriched with full-length mRNA that encodes a peptide or polypeptide for use in the delivery to or treatment of the lung of a subject or a lung cell. In certain embodiments the present invention provides a method for producing a therapeutic composition enriched with full-length mRNA that encodes for cystic fibrosis transmembrane conductance regulator (CFTR) protein. In certain embodiments the present invention provides a method for producing a therapeutic composition enriched with full-length mRNA that encodes for ATP-binding cassette sub-family A member 3 protein. In certain embodiments the present invention provides a method for producing a therapeutic composition enriched with full-length mRNA that encodes for dynein axonemal intermediate chain 1 protein. In certain embodiments the present invention provides a method for producing a therapeutic composition enriched with full-length mRNA that encodes for dynein axonemal heavy chain 5 (DNAH5) protein. In certain embodiments the present invention provides a method for producing a therapeutic composition enriched with full-length mRNA that encodes for alpha-1-antitrypsin protein. In certain embodiments the present invention provides a method for producing a therapeutic composition enriched with full-length mRNA that encodes for forkhead box P3 (FOXP3) protein. In certain embodiments the present invention provides a method for producing a therapeutic composition enriched with full-length mRNA that encodes one or more surfactant protein, e.g., one or more of surfactant A protein, surfactant B protein, surfactant C protein, and surfactant D protein.

In certain embodiments the present invention provides a method for producing a therapeutic composition enriched with full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition enriched with full-length mRNA that encodes for a protein associated with a urea cycle disorder. In certain embodiments the present invention provides a method for producing a therapeutic composition enriched with full-length mRNA that encodes for ornithine transcarbamylase (OTC) protein. In certain embodiments the present invention provides a method for producing a therapeutic composition enriched with full-length mRNA that encodes for arginosuccinate synthetase 1 protein. In certain embodiments the present invention provides a method, for producing a therapeutic composition enriched with full-length mRNA that encodes for carbamoyl phosphate synthetase I protein. In certain embodiments the present invention provides a method for producing a therapeutic composition enriched with full-length mRNA that encodes for arginosuccinate lyase protein. In certain embodiments the present invention provides a method for producing a therapeutic composition enriched with full-length mRNA that encodes for arginase protein.

In certain embodiments the present invention provides a method for producing a therapeutic composition enriched with full-length mRNA that encodes for a protein associated with a lysosomal storage disorder. In certain embodiments the present invention provides a method for producing a therapeutic composition enriched with full-length mRNA that encodes for alpha galactosidase protein. In certain embodiments the present invention provides a method for producing a therapeutic composition enriched with full-length mRNA that encodes for glucocerebrosidase protein. In certain embodiments the present invention provides a method for producing a therapeutic composition enriched with full-length mRNA that encodes for iduronate-2-sulfatase protein. In certain embodiments the present invention provides a method for producing a therapeutic composition enriched with full-length mRNA that encodes for iduronidase protein. In certain embodiments the present invention provides a method for producing a therapeutic composition enriched with full-length mRNA that encodes for N-acetyl-alpha-D-glucosaminidase protein. In certain embodiments the present invention provides a method for producing a therapeutic composition enriched with full-length mRNA that encodes for heparan N-sulfatase protein. In certain embodiments the present invention provides a method for producing a therapeutic composition enriched with full-length mRNA that encodes for galactosamine-6 sulfatase protein. In certain embodiments the present invention provides a method for producing a therapeutic composition enriched with full-length mRNA that encodes for beta-galactosidase protein. In certain embodiments the present invention provides a method for producing a therapeutic composition enriched with full-length mRNA that encodes for lysosomal lipase protein. In certain embodiments the present invention provides a method for producing a therapeutic composition enriched with full-length mRNA that encodes for arylsulfatase B (N-acetylgalactosamine-4-sulfatase) protein. In certain embodiments the present invention provides a method for producing a therapeutic composition enriched with full-length mRNA that encodes for transcription factor EB (TFEB).

In certain embodiments the present invention provides a method for producing a therapeutic composition enriched with full-length mRNA that encodes for a protein associated with a glycogen storage disorder. In certain embodiments the present invention provides a method for producing a therapeutic composition enriched with full-length mRNA that encodes for acid alpha-glucosidase protein. In certain embodiments the present invention provides a method for producing a therapeutic composition enriched with full-length mRNA that encodes for glucose-6-phosphatase (G6PC) protein. In certain embodiments the present invention provides a method for producing a therapeutic composition enriched with full-length mRNA that encodes for liver glycogen phosphorylase protein. In certain embodiments the present invention provides a method for producing a therapeutic composition enriched with full-length mRNA that encodes for muscle phosphoglycerate mutase protein. In certain embodiments the present invention provides a method for producing a therapeutic composition enriched with full-length mRNA that encodes for glycogen debranching enzyme.

In certain embodiments the present invention provides a method for producing a therapeutic composition enriched with full-length mRNA that encodes for a protein associated with amino acid metabolism. In certain embodiments the present invention provides a method for producing a therapeutic composition enriched with full-length mRNA that encodes for phenylalanine hydroxylase enzyme. In certain embodiments the present invention provides a method for producing a therapeutic composition enriched with full-length mRNA that encodes for glutaryl-CoA dehydrogenase enzyme. In certain embodiments the present invention provides a method for producing a therapeutic composition enriched with full-length mRNA that encodes for propionyl-CoA caboxylase enzyme. In certain embodiments the present invention provides a method for producing a therapeutic composition enriched with full-length mRNA that encodes for oxalase alanine-glyoxylate aminotransferase enzyme.

In certain embodiments the present invention provides a method for producing a therapeutic composition enriched with full-length mRNA that encodes for a protein associated with a lipid metabolism or fibrotic disorder. In certain embodiments the present invention provides a method for producing a therapeutic composition enriched with full-length mRNA that encodes for a mTOR inhibitor. In certain embodiments the present invention provides a method for producing a therapeutic composition enriched with full-length mRNA that encodes for ATPase phospholipid transporting 8B1 (ATP8B1) protein. In certain embodiments the present invention provides a method for producing a therapeutic composition enriched with full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition enriched with full-length mRNA that encodes for PPAR-gamma protein or an active variant.

In certain embodiments the present invention provides a method for producing a therapeutic composition enriched with full-length mRNA that encodes for a protein associated with methylmalonic acidemia. For example, in certain embodiments the present invention provides a method for producing a therapeutic composition enriched with full-length mRNA that encodes for methylmalonyl CoA mutase protein. In certain embodiments the present invention provides a method for producing a therapeutic composition enriched with full-length mRNA that encodes for methylmalonyl CoA epimerase protein.

In certain embodiments the present invention provides a method for producing a therapeutic composition enriched with full-length mRNA for which delivery to or treatment of the liver can provide therapeutic benefit. In certain embodiments the present invention provides a method for producing a therapeutic composition enriched with full-length mRNA that encodes for ATP7B protein, also known as Wilson disease protein. In certain embodiments the present invention provides a method for producing a therapeutic composition enriched with full-length mRNA that encodes for porphobilinogen deaminase enzyme. In certain embodiments the present invention provides a method for producing a therapeutic composition enriched with full-length mRNA that encodes for one or clotting enzymes, such as Factor VIII, Factor IX, Factor VII, and Factor X. In certain embodiments the present invention provides a method for producing a therapeutic composition enriched with full-length mRNA that encodes for human hemochromatosis (HFE) protein.

In certain embodiments the present invention provides a method for producing a therapeutic composition enriched with full-length mRNA that encodes a peptide or polypeptide for use in the delivery to or treatment of the cardiovasculature of a subject or a cardiovascular cell. In certain embodiments the present invention provides a method for producing a therapeutic composition enriched with full-length mRNA that encodes for vascular endothelial growth factor A protein. In certain embodiments the present invention provides a method for producing a therapeutic composition enriched with full-length mRNA that encodes for relaxin protein. In certain embodiments the present invention provides a method for producing a therapeutic composition enriched with full-length mRNA that encodes for bone morphogenetic protein-9 protein. In certain embodiments the present invention provides a method for producing a therapeutic composition enriched with full-length mRNA that encodes for bone morphogenetic protein-2 receptor protein.

In certain embodiments the present invention provides a method for producing a therapeutic composition enriched with full-length mRNA that encodes a peptide or polypeptide for use in the delivery to or treatment of the muscle of a subject or a muscle cell. In certain embodiments the present invention provides a method for producing a therapeutic composition enriched with full-length mRNA that encodes for dystrophin protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes a peptide or polypeptide for use in the delivery to or treatment of the cardiac muscle of a subject or a cardiac muscle cell. In certain embodiments the present invention provides a method for producing a therapeutic composition enriched with full-length mRNA that encodes for a protein that modulates one or both of a potassium channel and a sodium channel in muscle tissue or in a muscle cell. In certain embodiments the present invention provides a method for producing a therapeutic composition enriched with full-length mRNA that encodes for a protein that modulates a Kv7.1 channel in muscle tissue or in a muscle cell. In certain embodiments the present invention provides a method for producing a therapeutic composition enriched with full-length mRNA that encodes for a protein that modulates a Nav1.5 channel in muscle tissue or in a muscle cell.

In certain embodiments the present invention provides a method for producing a therapeutic composition enriched with full-length mRNA that encodes a peptide or polypeptide for use in the delivery to or treatment of the nervous system of a subject or a nervous system cell. For example, in certain embodiments the present invention provides a method for producing a therapeutic composition enriched with full-length mRNA that encodes for survival motor neuron 1 protein. For example, in certain embodiments the present invention provides a method for producing a therapeutic composition enriched with full-length mRNA that encodes for survival motor neuron 2 protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes for ATP binding cassette sub-family D member 1 (ABCD1) protein. In certain embodiments the present invention provides a method for producing a therapeutic composition enriched with full-length mRNA that encodes for CLN3 protein.

In certain embodiments the present invention provides a method for producing a therapeutic composition enriched with full-length mRNA that encodes a peptide or polypeptide for use in the delivery to or treatment of the blood or bone marrow of a subject or a blood or bone marrow cell. In certain embodiments the present invention provides a method for producing a therapeutic composition enriched with full-length mRNA that encodes for beta globin protein. In certain embodiments the present invention provides a method for producing a therapeutic composition enriched with full-length mRNA that encodes for Bruton's tyrosine kinase protein. In certain embodiments the present invention provides a method for producing a therapeutic composition enriched with full-length mRNA that encodes for one or clotting enzymes, such as Factor VIII, Factor IX, Factor VII, and Factor X.

In certain embodiments the present invention provides a method for producing a therapeutic composition enriched with full-length mRNA that encodes a peptide or polypeptide for use in the delivery to or treatment of the kidney of a subject or a kidney cell. In certain embodiments the present invention provides a method for producing a therapeutic composition enriched with full-length mRNA that encodes for collagen type IV alpha 5 chain (COL4A5) protein.

In certain embodiments the present invention provides a method for producing a therapeutic composition enriched with full-length mRNA that encodes a peptide or polypeptide for use in the delivery to or treatment of the eye of a subject or an eye cell. In certain embodiments the present invention provides a method for producing a therapeutic composition enriched with full-length mRNA that encodes for ATP-binding cassette sub-family A member 4 (ABCA4) protein. In certain embodiments the present invention provides a method for producing a therapeutic composition enriched with full-length mRNA that encodes for retinoschisin protein. In certain embodiments the present invention provides a method for producing a therapeutic composition enriched with full-length mRNA that encodes for retinal pigment epithelium-specific 65 kDa (RPE65) protein. In certain embodiments the present invention provides a method for producing a therapeutic composition enriched with full-length mRNA that encodes for centrosomal protein of 290 kDa (CEP290).

In certain embodiments the present invention provides a method for producing a therapeutic composition enriched with full-length mRNA that encodes a peptide or polypeptide for use in the delivery of or treatment with a vaccine for a subject or a cell of a subject. For example, in certain embodiments the present invention provides a method for producing a therapeutic composition enriched with full-length mRNA that encodes for an antigen from an infectious agent, such as a virus. In certain embodiments the present invention provides a method for producing a therapeutic composition enriched with full-length mRNA that encodes for an antigen from influenza virus. In certain embodiments the present invention provides a method for producing a therapeutic composition enriched with full-length mRNA that encodes for an antigen from respiratory syncytial virus. In certain embodiments the present invention provides a method for producing a therapeutic composition enriched with full-length mRNA that encodes for an antigen from rabies virus. In certain embodiments the present invention provides a method for producing a therapeutic composition enriched with full-length mRNA that encodes for an antigen from cytomegalovirus. In certain embodiments the present invention provides a method for producing a therapeutic composition enriched with full-length mRNA that encodes for an antigen from rotavirus. In certain embodiments the present invention provides a method for producing a therapeutic composition enriched with full-length mRNA that encodes for an antigen from a hepatitis virus, such as hepatitis A virus, hepatitis B virus, or hepatitis C virus. In certain embodiments the present invention provides a method for producing a therapeutic composition enriched with full-length mRNA that encodes for an antigen from human papillomavirus. In certain embodiments the present invention provides a method for producing a therapeutic composition enriched with full-length mRNA that encodes for an antigen from a herpes simplex virus, such as herpes simplex virus 1 or herpes simplex virus 2. In certain embodiments the present invention provides a method for producing a therapeutic composition enriched with full-length mRNA that encodes for an antigen from a human immunodeficiency virus, such as human immunodeficiency virus type 1 or human immunodeficiency virus type 2. In certain embodiments the present invention provides a method for producing a therapeutic composition enriched with full-length mRNA that encodes for an antigen from a human metapneumovirus. In certain embodiments the present invention provides a method for producing a therapeutic composition enriched with full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition enriched with full-length mRNA that encodes for an antigen from malaria virus. In certain embodiments the present invention provides a method for producing a therapeutic composition enriched with full-length mRNA that encodes for an antigen from zika virus. In certain embodiments the present invention provides a method for producing a therapeutic composition enriched with full-length mRNA that encodes for an antigen from chikungunya virus.

In certain embodiments the present invention provides a method for producing a therapeutic composition enriched with full-length mRNA that encodes for an antigen associated with a cancer of a subject or identified from a cancer cell of a subject. In certain embodiments the present invention provides a method for producing a therapeutic composition enriched with full-length mRNA that encodes for an antigen determined from a subject's own cancer cell, i.e., to provide a personalized cancer vaccine. In certain embodiments the present invention provides a method for producing a therapeutic composition enriched with full-length mRNA that encodes for an antigen expressed from a mutant KRAS gene.

In certain embodiments the present invention provides a method for producing a therapeutic composition enriched with full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition enriched with full-length mRNA that encodes for an antibody to OX40. In certain embodiments the present invention provides a method for producing a therapeutic composition enriched with full-length mRNA that encodes for an antibody to VEGF. In certain embodiments the present invention provides a method for producing a therapeutic composition enriched with full-length mRNA that encodes for an antibody to tissue necrosis factor alpha. In certain embodiments the present invention provides a method for producing a therapeutic composition enriched with full-length mRNA that encodes for an antibody to CD3. In certain embodiments the present invention provides a method for producing a therapeutic composition enriched with full-length mRNA that encodes for an antibody to CD19.

In certain embodiments the present invention provides a method for producing a therapeutic composition enriched with full-length mRNA that encodes for an immunomodulator. In certain embodiments the present invention provides a method for producing a therapeutic composition enriched with full-length mRNA that encodes for Interleukin 12. In certain embodiments the present invention provides a method for producing a therapeutic composition enriched with full-length mRNA that encodes for Interleukin 23. In certain embodiments the present invention provides a method for producing a therapeutic composition enriched with full-length mRNA that encodes for Interleukin 36 gamma. In certain embodiments the present invention provides a method for producing a therapeutic composition enriched with full-length mRNA that encodes for a constitutively active variant of one or more stimulator of interferon genes (STING) proteins.

In certain embodiments the present invention provides a method for producing a therapeutic composition enriched with full-length mRNA that encodes for an endonuclease. In certain embodiments the present invention provides a method for producing a therapeutic composition enriched with full-length mRNA that encodes for an RNA-guided DNA endonuclease protein, such as Cas 9 protein. In certain embodiments the present invention provides a method for producing a therapeutic composition enriched with full-length mRNA that encodes for a meganuclease protein. In certain embodiments the present invention provides a method for producing a therapeutic composition enriched with full-length mRNA that encodes for a transcription activator-like effector nuclease protein. In certain embodiments the present invention provides a method for producing a therapeutic composition enriched with full-length mRNA that encodes for a zinc finger nuclease protein.

Another aspect of the present invention is a purified mRNA composition prepared by an above-described aspect or embodiment.

Yet another aspect of the present invention is pharmaceutical composition including the purified mRNA composition of the above aspect and at least one pharmaceutically-acceptable excipient.

An aspect of the present invention is a method for treating a disease or disorder including a step of administering to a subject in need thereof the pharmaceutical composition of the above aspect.

Another aspect of the present invention is a solution including purified mRNA prepared by an above-described aspect or embodiment.

Yet another aspect of the present invention is a pharmaceutical composition including the solution including purified mRNA of the above aspect and at least one pharmaceutically-acceptable excipient.

An aspect of the present invention is a method for treating a disease or disorder including a step of administering to a subject in need thereof the pharmaceutical composition of the above aspect.

The present invention further includes a composition including a purified mRNA precipitate produced by an above aspect and/or embodiment.

The present invention further includes a pharmaceutical composition including a purified mRNA precipitate produced by an above aspect and/or embodiment and at least one pharmaceutically-acceptable excipient.

The present invention further includes a method for treating a disease or disorder comprising administering to a subject in need thereof a pharmaceutical composition of the above aspect and/or embodiment.

Any aspect or embodiment described herein can be combined with any other aspect or embodiment as disclosed herein. While the disclosure has been described in conjunction with the detailed description thereof, the above description is intended to illustrate and not limit the scope of the disclosure, which is defined by the scope of the appended claims. Other aspects, advantages, and modifications are within the scope of the following claims.

Additional teaching relevant to the present invention are described in one or more of the following: WO 2010/053572; WO 2011/068810; WO 2012/075040; WO 2012/170889; WO 2012/170930; WO 2013/063468; WO 2013/149140; WO 2013/149141; WO 2013/185067; WO 2013/185069; WO 2014/089486; WO 2014/152513; WO 2014/152659; WO 2014/152673; WO 2014/152774; WO 2014/152966; WO 2014/153052; WO 2015/061461; WO 2015/061467; WO 2015/061491; WO 2015/061500; WO 2015/148247; WO 2015/164773; WO 2015/184256; WO 2015/200465; WO 2016/004318; WO 2016/149508; WO/2014/152940; PCT/US16/57044; U.S. 62/320,073; U.S. 62/349,331; U.S. 62/420,413; U.S. 62/420,421; U.S. 62/420,428; U.S. 62/420,435; U.S. 62/421,007; U.S. 62/421,021, and the related applications filed Feb. 27, 2017 by Applicant entitled "LARGE SCALE SYNTHESIS OF MESSENGER RNA" (U.S. 62/464,043), "METHODS FOR PURIFICATION OF MESSENGER RNA" (U.S. 62/463,998), and "NOVEL CODON-OPTIMIZED CFTR MRNA" (U.S. 62/464,215), each of which is incorporated by reference in its entirety.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

Examples

Example 1: General Experimental Design

IVT Reaction:

RNA was in vitro transcribed (IVT) using the following exemplary procedures. Briefly, for each gram of mRNA transcribed, a reaction containing 8 mg of a linearized double stranded DNA plasmid with an RNA polymerase-specific promoter, RNA polymerase (e.g., SP6 polymerase or T7 polymerase), RNase inhibitor, pyrophosphatase, 29 mM NTPs, 10 mM DTT and a reaction buffer (10×-800 mM HEPES, 20 mM spirmidine, 250 mM MgCl, pH 7.7) was prepared and quantity sufficient (QS) to 179 ml with RNase-free water then incubated at 37° C. for 60 min. The reaction was then quenched by the addition of DNase I and a DNase I buffer (10×-100 mM Tris-HCl, 5 mM $MgCl_2$ and 25 mM $CaCl_2$, pH 7.6) to facilitate digestion of the double-stranded DNA template in preparation for purification. The final reaction volume was 204 ml.

Capping and Tailing (C/T) Reaction:

In vitro transcribed mRNA was modified enzymatically by the addition of a 5' $N^7$-methylguanylate Cap 0 structure using guanylate transferase and the addition of a methyl group at the 2' 0 position of the penultimate nucleotide resulting in a Cap 1 structure using 2' O-methyltransferase as described by (Fechter, P.; Brownlee, G. G. "Recognition of mRNA cap structures by viral and cellular proteins" J. Gen. Virology 2005, 86, 1239-1249). Following addition of the Cap 1 structure, a poly-adenylate tail was added to the 3' end of the in vitro transcribed mRNA enzymatically using poly-A polymerase. Briefly, a capping reaction was set up for every gram of purified IVT containing 2.5 mM GTP, 246 µM S-adenosyl methionine, RNase inhibitor, 2'-Omethyl transferase, guanylyl transferase, a reaction buffer (10×-500 mM Tris-HCl pH 8.0, 60 mM $MgCl_2$, and 12.5 mM $MgCl_2$) and QS to 650 ml with RNase-free $H_2O$ then incubated at 37° C. for 60 minutes. Following the incubation, a tailing reaction was initiated by adding tailing buffer (10×-500 mM Tris-HCl pH 8.0, 2.5 M NaCl, 100 mM $MgCl_2$), 3.7 mM ATP, poly-A polymerase and QS to 800 ml with RNase-free $H_2O$. The tailing reaction was carried out at 37° C. for 30 minutes before the addition of 12.5 mM EDTA to quench.

RNA Precipitation:

Generally, for every gram of mRNA (IVT reaction, C/T reaction, or previously-purified aqueous mRNA) salt-EtOH precipitations were performed as follows. The mRNA was brought to 1 g/l using RNase-free $H_2O$ and then an equal volume of GSCN buffer containing 4M guanidine thiocynate, 25 mM sodium citrate pH 6.5 and 0.5% N-lauroylsarcosine was added. The mRNA solution was mixed thoroughly and incubated at ambient temperature for five minutes with continual mixing. An equal volume of absolute ethanol was then added to the mRNA-GSCN solution and continuously mixed for 5 minutes at ambient temperature to facilitate precipitation.

Figure 2:
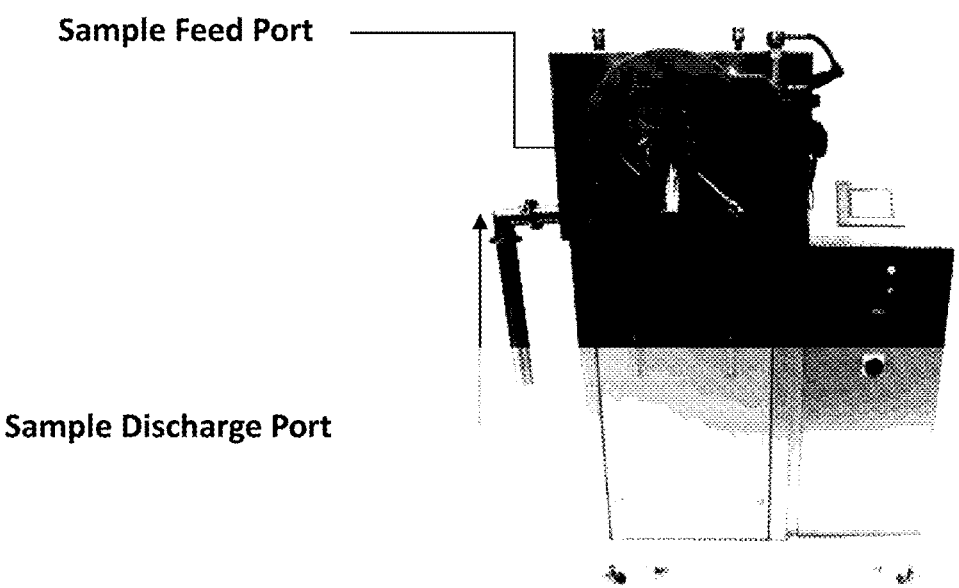
FIG. 2 is a photograph of a kilogram-scale horizontal filtering peeler centrifuge with a 300 mm basket (1400 $cm^2$).

Centrifuge Set-Up:

A vertical filtering centrifuge with a six inch basket and 438 $cm^2$ filter surface area or a horizontal filtering peeler centrifuge with a 300 mm basket and 1400 $cm^2$ filter surface area (FIG. 1 and FIG. 2, respectively) was prepared as follows. The vertical filtering centrifuge bowl was prepared by placing a filter paper on the inside of the six inch centrifuge basket. The horizontal centrifuge bowl was prepared by placing multiple filter papers on the inside of the 300 mm basket followed by a custom, one micron polypropylene peeler cloth with welded rope filter basket. For either centrifuge, tubing was connected to the sample feed and the discharge port. The sample feed tubing was run through a peristaltic pump and into a ten liter TFF vessel and the sample discharge tubing was run through a peristaltic pump and into a twenty liter waste vessel. The centrifuge was started at 3000 RPM and sanitized with five liters of 0.1N NaOH feed through the feed port at four liters per minute and removed via the discharge port with the discharge pump set to 550 RPM. The system was then neutralized with five washes of five liters $H_2O$ following the same load and removal method.

RNA Analytics

RNA integrity (which includes poly-A tail length for C/T samples) was analyzed using the CE Fragment Analyzer™ with standard sensitivity mRNA analysis kit (Advanced Analytical Tech.) with a total mRNA load of 300 ng. Residual process enzymes were analyzed by preparing 20 µg of RNase I digested mRNA in NuPAGE sample loading and reducing buffer, separating samples on a NuPage 10% bis-tris gel at 200V for 35 minutes (Invitrogen). Then residual proteins were visualized using the SilverQuest™ silver stain kit (Invitrogen). Luciferase activity was measured in mice dosed with FFL mRNA purified according to the present invention and formulated with a proprietary lipid nanoparticle followed by Flux intensity captured on IVIS Imager system twenty-four hours after dosing and after administration of the luciferase substrate, luciferin.

Recovered Amounts of mRNA

The starting mass of an mRNA to be purified is calculated based on the theoretically expected amount of product as determined by initial reagent amounts in an IVT and/or a cap/tail reaction used to prepare the mRNA to be purified. The percent yield is calculated as the ratio of the obtained product to the theoretically expected amount of product.

Long-Term Storage

Purified mRNA obtained according to methods described herein can be stored as a dried solid (e.g., following separation from a filter) at low temperatures (e.g., below 0° C. such as about −20° C.) for periods of time of at least about 1-24 months or for a period of time that is about one week to about 24 months.

Example 2: One Gram to Three Gram mRNA Purification

Method 1: Vertical centrifuge, one gram FFL CR' Reaction Purification ($H_2O$ Elution)

A one gram Firefly Luciferase (FFL) CIT reaction was carried out as described above. Following DNase I treatment, the one gram reaction was QS to one liter with RNase-free $H_2O$ and precipitated with equal volumes of GSCN buffer and EtOH (see above) then loaded onto a vertical filtering centrifuge through the sample feed port with centrifuge set to 3000 RPM until all precipitate was captured. The mRNA precipitate collected on the centrifuge filter was washed with two liters of GSCN-EtOH wash solution (57.6% GSCN and 42.4% EtOH) with centrifuge at 3000 RPM. The mRNA precipitate was then washed with ten liters of 80% EtOH and again loaded through the sample feed port with centrifuge remaining at 3000 RPM. The mRNA precipitate was dried for ten minutes while spinning at 3000 RPM with all ports open to ambient conditions. The mRNA was then suspended in $H_2O$ as follows. The centrifuge was left at 3000 RPM, one liter of $H_2O$ was added to the centrifuge basket through the sample feed port and the filtrate ($RNA/H_2O$) was returned to the elution vessel via the sample discharge port for recirculation. Recirculation continued for fifteen minutes before the one liter elution was collected and the concentration of mRNA was determined by measuring absorbance at 260 nm.

Method 2: Vertical Centrifuge, Two Gram FFL IVT Reaction Purification ($H_2O$ Elution)

A two gram Firefly Luciferase (FFL) IVT reaction was carried out as described above. Following DNase I treatment, the two gram reaction was QS to one liter with RNase-free $H_2O$ and precipitated with equal volumes of GSCN buffer and EtOH (see above) then loaded onto a vertical filtering centrifuge through the sample feed port with centrifuge set to 3000 RPM until all precipitate was captured. The mRNA precipitate collected on the centrifuge filter was washed with 2.5 liters of GSCN-EtOH wash solution (57.6% GSCN and 42.4% EtOH) through the sample feed port with centrifuge at 3000 RPM. The mRNA precipitate was then washed with ten liters of 80% EtOH and again loaded through the sample feed port with centrifuge remaining at 3000 RPM. The mRNA precipitate was dried for ten minutes while spinning at 3000 RPM with all ports open to ambient conditions. The mRNA was then suspended in $H_2O$ as follows. The centrifuge was left at 3000 RPM, one liter of $H_2O$ was added to the centrifuge basket through the sample feed port and the filtrate ($mRNA/H_2O$) was returned to the elution vessel via the sample discharge port for recirculation (Elution Wash #1). Recirculation continued for thirty minutes before the entire one liter elution was collected and the concentration of mRNA was determined by measuring absorbance at 260 nm. A second one liter $H_2O$ elution was performed as described with Elution Wash #1 but after five minutes of recirculation the second one liter elution was collected (Elution Wash #2) and the mRNA concentration was determined by measuring absorbance at 260 nm. The total mRNA yield of 95% was calculated based on the total quantity of purified mRNA recovered as compared to the starting quantity of mRNA (see Table 1).

Method 3: Vertical Centrifuge, Three Gram FFL Luciferase mRNA ($H_2O$ Elution):

Three grams of previously-purified Firefly luciferase (FFL) C/T mRNA was QS to two liters with RNase-free $H_2O$ and precipitated with equal volumes of GSCN buffer and EtOH (see above) then loaded onto a vertical filtering centrifuge at a rate of 0.5 liter/min through the sample feed port with centrifuge set to 3000 RPM. The mRNA precipitate collected on the centrifuge filter was washed with 2.5 liters of GSCN-EtOH wash solution (57.6% GSCN and 42.4% EtOH) through the sample feed port with centrifuge at 3000 RPM. The mRNA precipitate was then washed with ten liters of 80% EtOH through the sample feed port with centrifuge remaining at 3000 RPM. The mRNA precipitate was dried for ten minutes while spinning at 3000 RPM with all ports open to ambient conditions. The mRNA was then suspended in $H_2O$ as follows. The centrifuge was left at 3000 RPM, two liters of $H_2O$ was added to the centrifuge basket through the sample feed port and the filtrate ($mRNA/H_2O$) was returned to the elution vessel via the sample discharge port for recirculation. Recirculation continued for fifteen minutes before the two liter elution was collected (Elution Wash #1) and the concentration of mRNA was determined by measuring absorbance at 260 nm. The total mRNA yield of 97% was calculated based on the total quantity of purified mRNA recovered as compared to the starting quantity of mRNA (see Table 1).

At this scale, the current precipitation, capture via filtering centrifugation, product wash and ultimate suspension of the purified mRNA target (firefly luciferase (FFL)) resulted in yield recoveries ranging from 95% to 97% (see Table 1).

TABLE 1

Elution and Recovery Summary for Centrifuge mRNA Purification

| Description of Centrifuge Purification | Elution Wash Number | Elution Time (min) | Elution Wash Volume (L) | mRNA Concentration (g/L) | Yield (g) | % Recovery |
|---|---|---|---|---|---|---|
| 2 grams of mRNA[1] | #1 | 30 | 1.0 | 1.80 | 1.8 | 90 |
|  | #2 | 5 | 1.0 | 0.12 | 0.1 | 5 |
|  | Totals | 35 | 2.0 |  | 1.9 | 95 |
| 3 grams of mRNA[2] | #1 | 15 | 2.0 | 1.44 | 2.9 | 97 |
|  | Totals | 15 | 2.0 |  | 2.9 | 97 |
| 10 grams of mRNA[3] | #1 | 60 | 2.9 | 2.1 | 6.1 | 61 |
|  | #2 | 60 | 3.0 | 1.3 | 3.9 | 39 |
|  | Totals | 120 | 5.9 |  | 10.0 | 100 |
| 10 grams of mRNA[4] | #1 | 30 | 5 | 1.12 | 5.5 | 55 |
|  | #2 | 30 | 5 | 0.69 | 3.5 | 35 |
|  | #3 | 15 | 2 | 0.32 | 0.6 | 6 |
|  | Totals | 75 | 12 |  | 9.6 | 96 |
| 100 grams of mRNA[4] |  | 3 days (4320 min) | 50 | 1.9 | 95 | 95 |

[1]FFL mRNA following IVT reaction, as described in Example 2, Method 2
[2]FFL mRNA following capping and tailing reaction (C/T), as described in Example 2, Method 3
[3]CFTR mRNA following capping and tailing reaction (C/T) and using a vertical centrifuge, as described in Example 3, Method 1
[4]CFTR mRNA following capping and tailing reaction (C/T) and using a horizontal centrifuge, as described in Example 3, Method 3
[5]CFTR mRNA following IVT reaction, as described in Example 5

Figure 3:
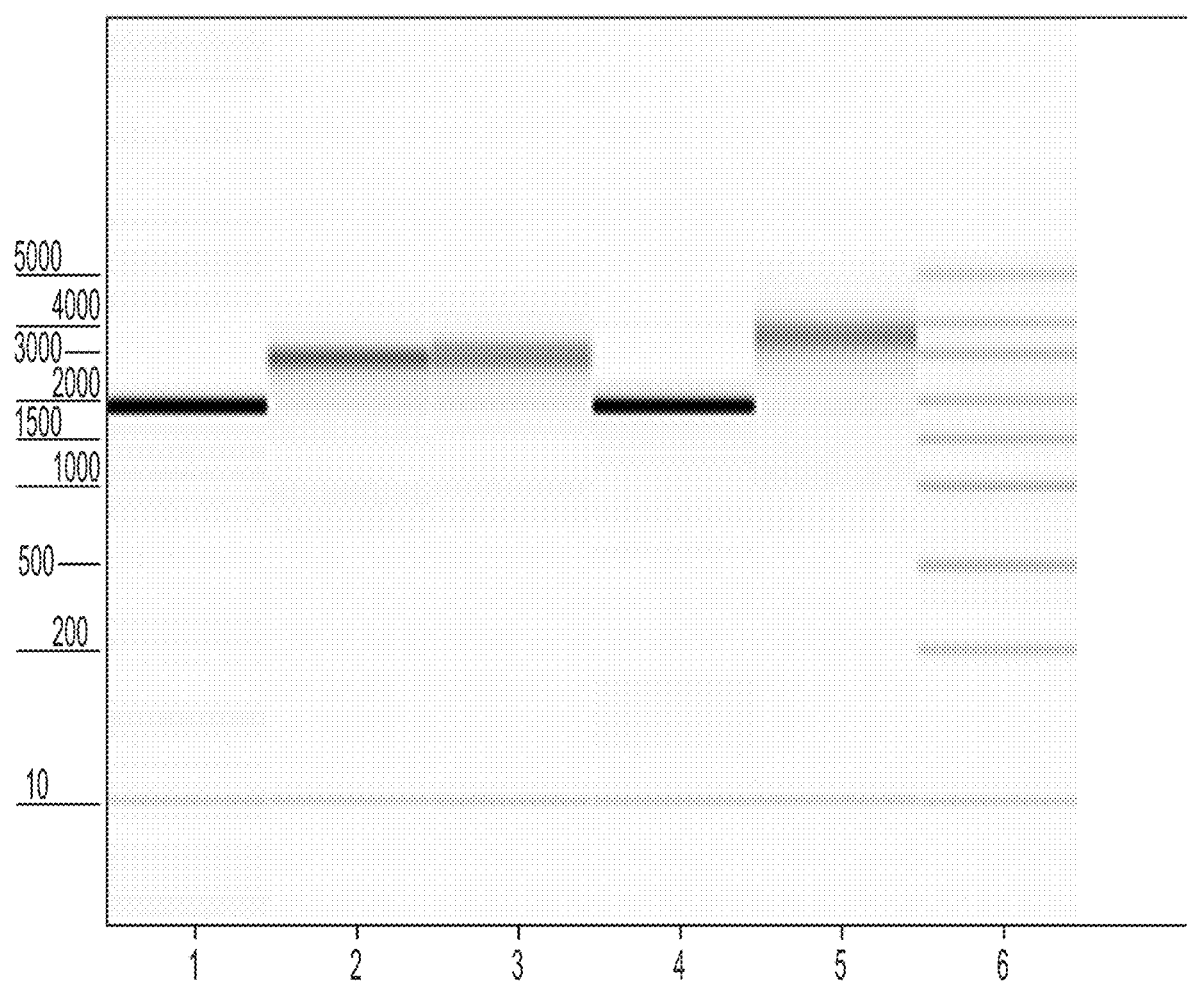
FIG. 3 is a digital image of a CE Fragment Analyzer™ gel for Firefly Luciferase (FFL) mRNA samples purified from one, two, or three gram batches. The one gram FFL Cap and Tail (C/T) reaction product purified using the present invention is shown in lane 2. The two gram in vitro transcription (IVT) reaction product purified using the present invention is shown in lane 1. The three gram FFL C/T reaction product which was twice purified using the present invention is shown in lane 3. Control FFL IVT and C/T reaction products, which were purified using a Qiagen® kit, are respectively shown in lanes 4 and 5.

CE Fragment Analyzer™ gel image analysis of the filtering centrifuge FFL mRNA revealed single defined bands of the appropriate molecular weight for the one, two, and three gram experiments (FIG. 3, lanes 1, 2, 3). The bands were equivalent to Qiagen® purified FFL controls (FIG. 3, lanes 4, 5).

Figure 4:
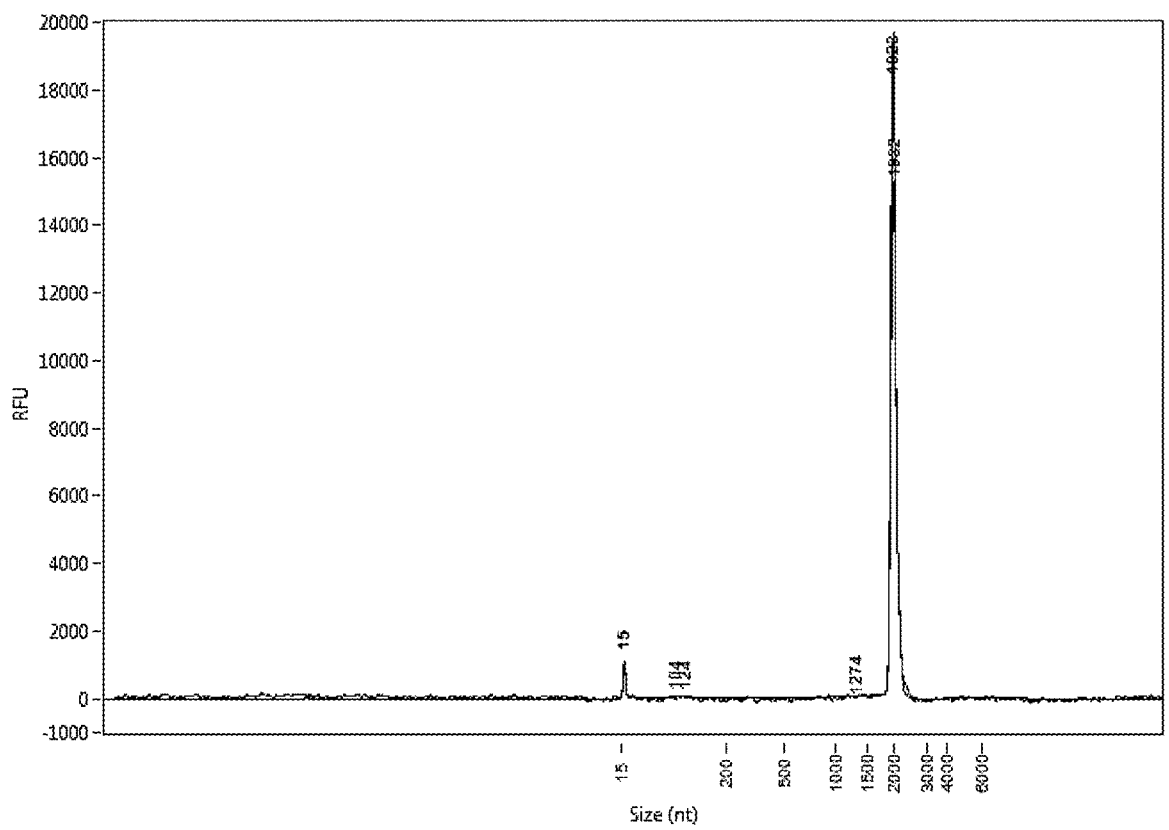
FIG. 4 is a graph of a CE Fragment Analyzer™ electropherogram showing a two gram FFL IVT reaction product purified using the present invention (in blue) and a control IVT reaction product purified using a Qiagen® kit (in black).

The CE Fragment Analyzer™ electropherogram of FIG. 4 compares the two gram IVT reaction FFL mRNA purified according to the present invention to a Qiagen® purified control (blue and black, respectively). The data shows that both samples exhibit similar size, peak profiles, and intensities.

Figure 5:
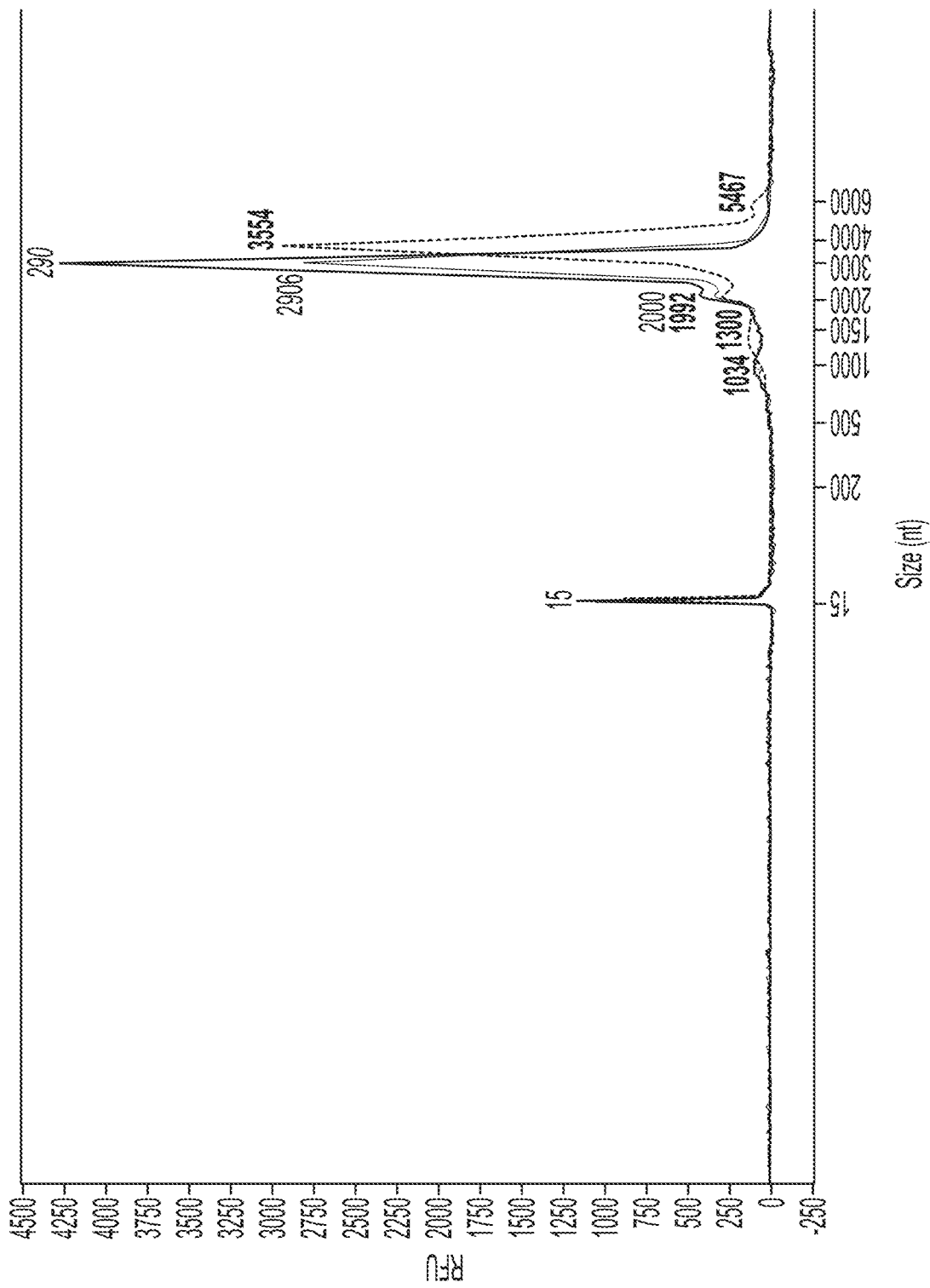
FIG. 5 is a graph of a CE Fragment Analyzer™ electropherogram showing one and two gram FFL C/T mRNA reaction products purified using the present invention (respectively, black and blue) and a control FFL C/T mRNA reaction product purified using a Qiagen® kit (red, Lot 8079-128).

Likewise, the CE Fragment Analyzer™ electropherogram of FIG. 5 compares the one and two gram C/T FFL mRNA purified according to the present invention to a Qiagen® purified control (black and blue versus red). The data shows that all samples exhibit similar peak profile and intensities while size differences, measured by peak location along the x-axis, are attributed to differences in poly-A tail lengths of the C/T mRNA. These data show that mRNA samples purified according to the present invention exhibit a single-defined band of the appropriate size and intensity when compared to control samples.

Figure 6:
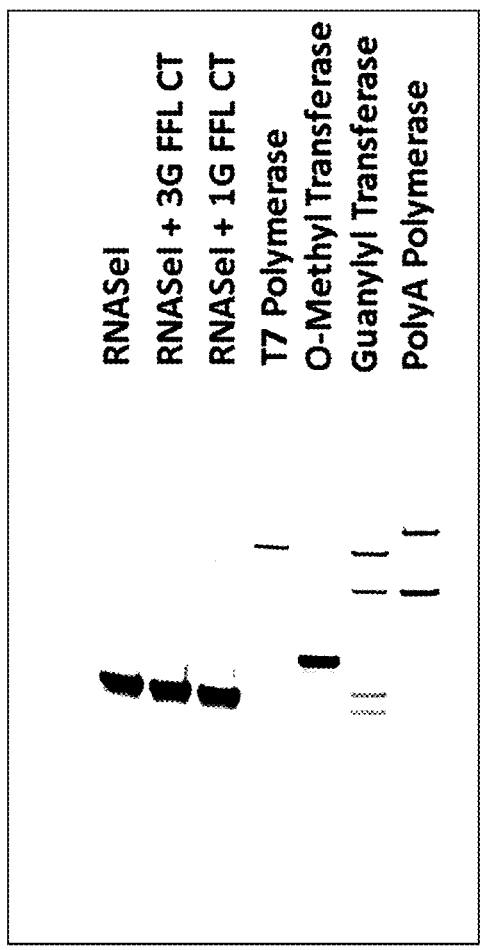
FIG. 6 is a digital image of a SilverQuest™ silver stain gel showing residual process enzymes in a one gram FFL C/T sample (lane 3) and no detectable process enzymes in a three gram FFL C/T sample (lane 2), each sample purified using the present invention. Lanes 1, 4, 5, 6, and 7 are process enzyme only controls.

The size of the non-C/T IVT FFL sample was nearly identical to the Qiagen® purified FFL mRNA sample. Further analysis of the SilverQuest™ silver stain gel image reveals that after a second round of purification (FIG. 6, lane 2 versus lane 3), the C/T FFL mRNA purified by the present invention exhibited removal of detectable levels of all process enzymes. These data show the present invention is capable of preparing purified mRNA which lacks detectable levels of process enzymes.

Figure 7:
FIG. 7 includes photographs of IVIS Live Animal Images. The animal on the right ("Treated") was dosed with FFL mRNA purified using the present invention and formulated with proprietary lipid nanoparticle and administered via topical eye drops. Images were captured on IVIS Imager after IVT luciferin injection.
Figure 7:
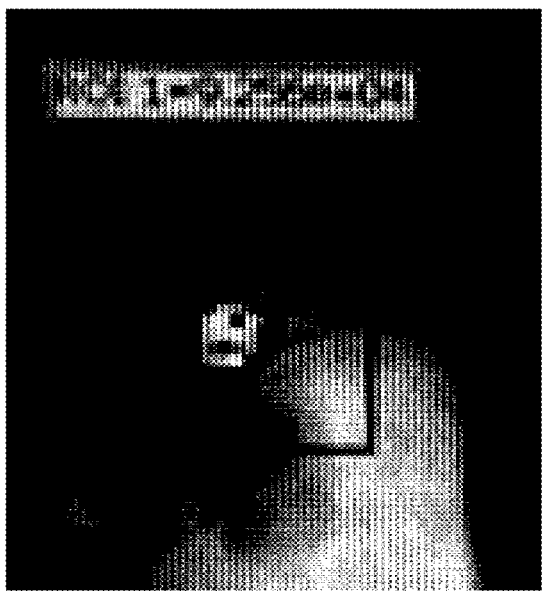

Finally, the FFL C/T mRNA (purified using the present invention) was formulated with a proprietary lipid nanoparticle and dosed to via topical eye drops to animals. Twenty-four hours after dosing, mice were administered luciferin via IVT injection and luciferase activity was measured and imaged on the IVIS Lumina. A significant Flux signal was observed with a group mean of 62193 p/s (See, Table 1 and FIG. 7) demonstrating successful production of active protein from mRNA purified using such methods. These data show mRNA purified using centrifugation can be efficiently be translated, in vivo, into functional proteins.

Together, these data demonstrate that the centrifuge based purification method described herein may be used to efficiently purify high quality mRNA resulting in yield recoveries, integrity profiles, purity and functionality equivalent to the industry-standard Qiagen® small scale mRNA purification method. Moreover, the present invention has a significant added benefit of scalability which is unavailable with the existing industry-standard methods and kits.

Example 3: Ten Gram Scale mRNA Purification

Method 1: Vertical Centrifuge, Ten Gram CFTR mRNA Purification ($H_2O$ Elution):

Ten grams of Cystic Fibrosis Transmembrane Receptor (CFTR) mRNA was synthesized using SP6 polymerase according to the IVT reaction and capping and tailing (C/T) reaction as described in Example 1 above.

The resulting CFTR C/T mRNA was QS to ten liters with RNase-free $H_2O$ and precipitated with equal volumes of GSCN buffer and EtOH (see above) then loaded onto the vertical filtering centrifuge through the sample feed port with centrifuge set to 3000 RPM. The mRNA precipitate collected on the centrifuge filter was washed with five liters of GSCN-EtOH wash solution (57.6% GSCN and 42.4% EtOH) through the sample feed port with centrifuge running at 3000 RPM. The mRNA precipitate was then washed with ten liters of 80% EtOH through the sample feed port with centrifuge remaining at 3000 RPM. The mRNA precipitate was dried for fifteen minutes while spinning at 3000 RPM with all ports open to ambient conditions. The mRNA was then suspended in H$_2$O as follows. The centrifuge was left at 3000 RPM, 2.9 liters of H$_2$O was added to the centrifuge basket through the sample feed port and the filtrate (RNA/H$_2$O) was returned to the elution vessel via the sample discharge port for recirculation. Recirculation continued for sixty minutes before the three liter elution was collected (Elution Wash #1) and the concentration of mRNA was determined by measuring absorbance at 260 nm. A second elution was performed with three liters of H$_2$O, as described for Elution Wash #1; following sixty minutes of recirculation, the second elution was collected (Elution Wash #2) and the mRNA concentration was determined by measuring absorbance at 260 nm. The total mRNA yield of 100% was calculated based on the total quantity of purified mRNA collected compared to the starting quantity of mRNA (see Table 1).

Method 2: Vertical Centrifuge, Ten Gram OTC IVT Reaction (Dry mRNA Purification Collection):

A ten gram ornothine transcarbamylase (OTC) IVT reaction was carried out using SP6 polymerase as described above. Following DNase I treatment, the ten gram reaction was QS to three liters with RNase-free H$_2$O and precipitated with equal volumes of GSCN buffer and EtOH (see above) then loaded onto the vertical filtering centrifuge through the sample feed port with centrifuge set to 3000 RPM. The mRNA precipitate collected on the centrifuge filter was washed with five liters of GSCN-EtOH wash solution (57.6% GSCN and 42.4% EtOH) through the sample feed port with centrifuge running at 3000 RPM. The mRNA precipitate was then washed with ten liters of 80% EtOH through the sample feed port with centrifuge remaining at 3000 RPM. The mRNA precipitate was dried for thirty minutes while spinning at 3000 RPM with all ports open to ambient conditions. The dried mRNA precipitate was manually harvested from the filter membrane, sectioned into manageable pieces and stored in a 250 ml sterile bottle at −20° C. for long-term storage.

Method 3: Horizontal Centrifuge, Ten Gram CFTR mRNA Purification (H$_2$O Elution):

Ten grams of IVT Cystic Fibrosis Transmembrane Receptor (CFTR) C/T mRNA according to the IVT reaction and capping and tailing (C/T) reaction as described in Example 1 above. The mRNA then was QS to ten liters with RNase-free H$_2$O and precipitated as describe above but with a ratio of 1 mRNA:2.3 GSCN Buffer:1.7 100% EtOH then loaded onto the Horizontal filtering centrifuge through the sample feed port with centrifuge set to 2750 RPM. The mRNA precipitate collected on the centrifuge filter was washed with ten liters of 80% EtOH through the sample feed port with centrifuge at 2500 RPM. The mRNA precipitate was dried for fifteen minutes while spinning at 2500 RPM with all ports open to ambient conditions. The mRNA was then suspended in H$_2$O as follows. The centrifuge was left at 2500 RPM, five liters of H$_2$O was added to the centrifuge basket through the sample feed port and the filtrate (RNA/H$_2$O) was returned to the elution vessel via the sample discharge port for recirculation. Recirculation continued for thirty minutes before the five liters elution was collected (Elution Wash #1) and the concentration of mRNA was determined by measuring absorbance at 260 nm. A second five liters elution was performed as described for Elution Wash #1 and following thirty minutes of recirculation, the second elution was collected (Elution Wash #2) and the mRNA concentration was determined by measuring absorbance at 260 nm. A final two liter elution was performed under the same conditions and collected (Elution Wash #3) after fifteen minutes of recirculation. Again, the mRNA concentration was determined by measuring absorbance at 260 nm. The total mRNA yield of 96% was calculated based on the total quantity of purified mRNA collected compared to the starting quantity of mRNA (see Table 1).

This example demonstrates that both vertical and horizontal filtering centrifuges can effectively capture and purify mRNA.

Analysis of the yield summary in Table 1 for the ten gram CFTR mRNA purified with a vertical centrifuge (see footnote 3) and the ten gram CFTR mRNA purified with a horizontal centrifuge (see footnote 4) revealed a percent recoveries of 100% and 96%, respectively.

Also conducted here was alternate harvest method where, following the final wash and drying step, the mRNA was collected by manual removal of the dried precipitated mRNA from the filter membrane with subsequent storage at −20° C. (data not shown).

Together, these data demonstrate the centrifuge based purification method according to the present invention can efficiently capture an purify at least ten grams of precipitated mRNA at a level of purity and integrity acceptable for therapeutic use, e.g., in a Clinical Study. The ability of the filtering centrifuge to provide two distinct mRNA harvest methods affords the researcher or clinician the ability to either continue processing the mRNA in an aqueous real time manner or to store the solid precipitate for long-term needs at a significantly reduced sample volume size.

Example 4: Fifty Gram Scale mRNA Purification

Fifty grams of IVT Cystic Fibrosis Transmembrane Receptor (CFTR) C/T mRNA was synthesized according to the IVT reaction and capping and tailing (C/T) reaction as described in Example 1 above. The mRNA reaction product then was QS to ten liters with RNase-free H$_2$O and precipitated with equal volumes of GSCN buffer and EtOH (see above) then loaded onto the vertical filtering centrifuge through the sample feed port with centrifuge set to 3000 RPM. The mRNA precipitate collected on the centrifuge filter was washed with five liters of GSCN-EtOH wash solution (57.6% GSCN and 42.4% EtOH) through the sample feed port with centrifuge running at 3000 RPM. The mRNA precipitate was then de-salted with a twenty liter 80% EtOH wash through the sample feed port with centrifuge remaining at 3000 RPM. The mRNA precipitate was dried for thirty minutes while spinning at 3000 RPM with all ports open to ambient conditions. The dried mRNA precipitate was manually harvested from the filter membrane, sectioned into manageable pieces and stored in a 500 ml sterile bottle at −20° C. for long term storage.

These data demonstrate the filtering centrifuges ability to capture and purify fifty grams of precipitated mRNA in a single batch.

Example 5: One-Hundred Gram Scale mRNA Purification

A one-hundred gram Cystic Fibrosis Transmembrane Receptor (CFTR) IVT reaction was carried out using SP6 RNA polymerase according to the IVT reaction as described in Example 1 above. The quenched reaction was QS to twenty liters with RNase-free H$_2$O and precipitated with equal volumes of GSCN buffer and EtOH (see above) then loaded onto a vertical filtering centrifuge through the sample feed port with centrifuge set to 3000 RPM. The mRNA precipitate collected on the centrifuge filter was washed with five liters of GSCN-EtOH wash solution (57.6% GSCN and 42.4% EtOH) through the sample feed port with centrifuge running at 3000 RPM. The mRNA precipitate was then washed with a fifty liter 80% EtOH wash through the sample feed port with centrifuge remaining at 3000 RPM. The mRNA precipitate was dried for thirty minutes while spinning at 3000 RPM with all ports open to ambient conditions. The dried mRNA precipitate was manually harvested from the filter membrane, sectioned into manageable pieces and stored in a two liter sterile bottle at −20° C. for long term storage.

Figure 11:
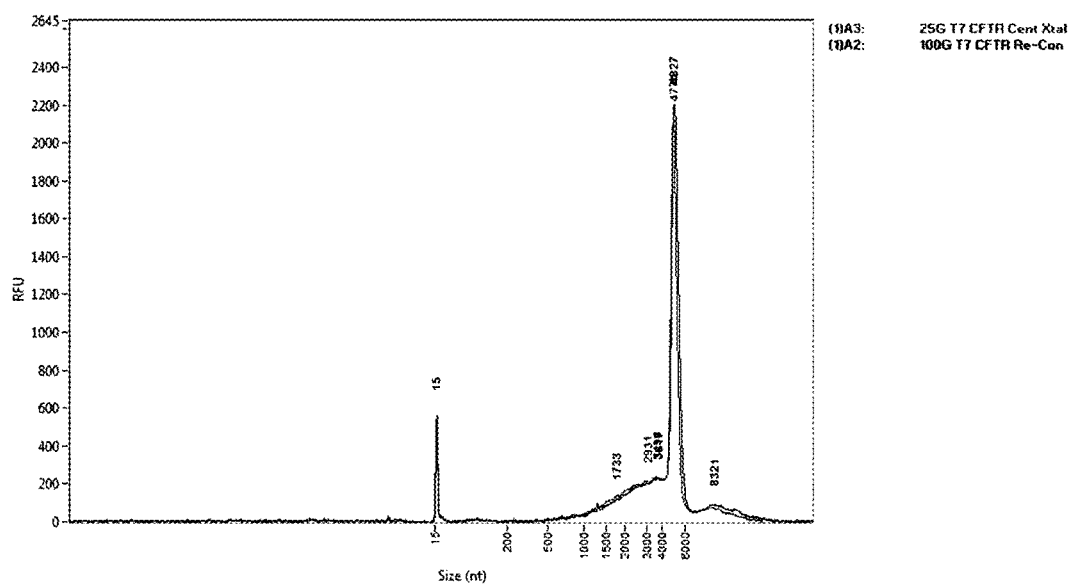
FIG. 11 depicts an electropherogram comparing mRNA encoding CFTR and which has been reconstituted following twelve months in dry storage at −20° C. to a recently-prepared batch of mRNA encoding CFTR.

Twelve months later, the mRNA was reconstituted, over 3 days, in fifty liters of $H_2O$ in a jacketed stainless steel vessel with chiller set at 10° C. The concentration of the reconstituted mRNA solution was determined by measuring absorbance at 260 nm. The total mRNA yield was calculated and compared to the theoretical yield based on the reaction scale. As shown in FIG. 11, an electropherogram of the reconstituted mRNA is substantially similar to a recently-prepared batch of mRNA encoding CFTR.

This example demonstrates that the filtering centrifuge was capable of capturing one-hundred grams of precipitated mRNA in a single batch. Following long term storage, reconstituted mRNA shows 95% recovery of the mRNA (see, Table 1, footnote 5).

These data demonstrate the filtering centrifuges ability to capture one-hundred grams of precipitated mRNA in a single batch.

Example 6: Purification of >20 Grams mRNA

The present example describes a large-scale purification of a batch of Cystic Fibrosis Transmembrane Receptor (CFTR) mRNA.

CFTR mRNA was synthesized using SP6 RNA polymerase according to the IVT reaction as described in Example 1 above. The mRNA reaction product then was subjected to an initial precipitation and purification using a horizontal centrifuge (H300P) in the presence of 250 g of filtration aid (Solka-Floc® 100NF powdered cellulose fiber) yielded 22 grams of CFTR mRNA, which was then further purified using dialysis to yield with no measurable loss of mRNA.

The obtained CFTR mRNA was then capped and tailed according to capping and tailing (C/T) reaction as described in Example 1 above, which yielded 21.8 grams CFTR C/T mRNA. The C/T mRNA was diluted to 10 L and then initially purified using a horizontal centrifuge (H300P) in the presence of 250 g of cellulose filtration aid (Solka-Floc® 100NF) to yield 21.8 grams C/T mRNA. The obtained mRNA was then further purified using dialysis to yield an initial amount of 21.1 grams of CFTR mRNA ("CFTR.6.1").

Obtained CFTR mRNA ("CFTR 6.1") was pooled and then concentrated to 1.9 g/L (18.67 g mRNA). The mRNA was then purified with a horizontal centrifuge (H300P; 50 L) in the presence of 250 g of cellulose filtration aid (Solka-Floc® 100NF), and 17.5 g mRNA was obtained. The mRNA was then further purified using dialysis, to provide a final yield of 16.5 g mRNA ("CFTR.6.2").

Figure 8:
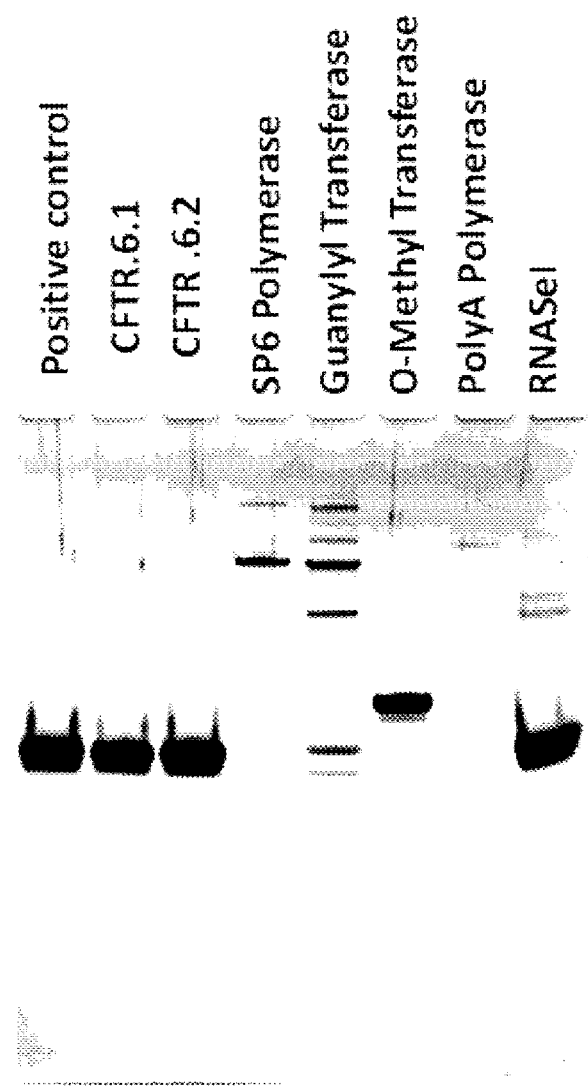
FIG. 8 depicts a SilverQuest™ silver stain gel comparing residual process enzymes in a sample of CFTR mRNA (lane 2) and a sample of CFTR mRNA purified according to Example 6 (lane 3).

Residual proteins were visualized by gel electrophoresis using SilverQuest™ silver stain as described above in Example 1, and results are shown in FIG. 8. FIG. 8 includes the final mRNA purified according to this example (lane 3) and shows that the present method can successfully reduce enzyme impurities in a large scale mRNA preparation as would be required for mRNA suitable for therapeutic uses.

Example 7: Purification of >30 Grams mRNA

The present example describes a large-scale purification of a batch of Cystic Fibrosis Transmembrane Receptor (CFTR) mRNA.

CFTR mRNA was transcribed using SP6 RNA polymerase according to the IVT reaction as described in Example 1 above. The mRNA reaction product was then subjected to an initial precipitation and purification using a horizontal centrifuge (H300P) in the presence of 500 g of cellulose filtration aid (Solka-Floc® 100NF) yielded 49.5 g of CFTR mRNA, which was then further purified using dialysis to yield 44.7 g mRNA.

The obtained mRNA was then capped and tailed according to capping and tailing (C/T) reaction as described in Example 1 above. The 44.7 grams of C/T mRNA was then diluted to 10 L, prior to initial purification using a horizontal centrifuge (H300P) in the presence of 500 g of cellulose filtration aid (Solka-Flcc® 100NF) followed by dialysis to yield 37.3 grams CFTR C/T mRNA ("CFTR.7.1").

The obtained C/T mRNA CFTR.7.1 was then pooled and concentrated to about 2 g/L (18.67 g mRNA). The mRNA was purified with a horizontal centrifuge (H300P; 100 L) in the presence of 500 g of cellulose filtration aid (Solka-Floc® 100NF), and 33.7 g mRNA was obtained. The mRNA was then further purified using dialysis, to provide a final yield of 32.6 g mRNA ("CFTR.7.2").

Figure 9A:
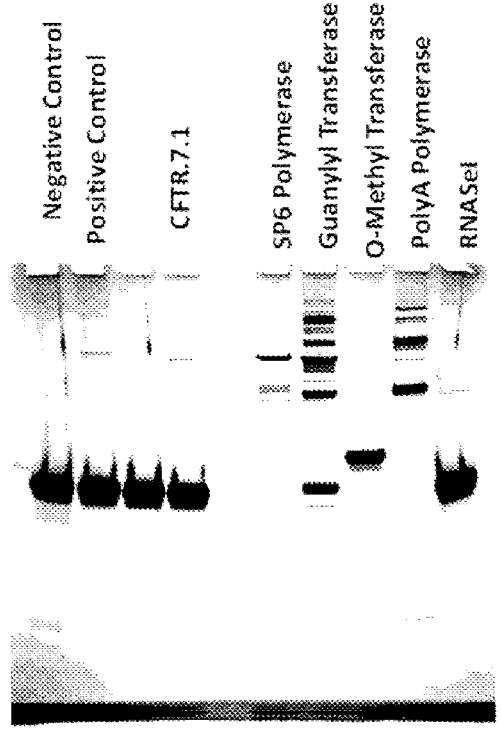
FIG. 9B depicts a SilverQuest™ silver stain gel comparing residual process enzymes in a sample of CFTR mRNA. As shown in these two figures, the mRNA purified according to Example 7 (FIG. 9B, lane 3) comprises fewer enzyme impurities as compared to the initial batch of mRNA (FIG. 9A, lane 4).
Figure 9B:
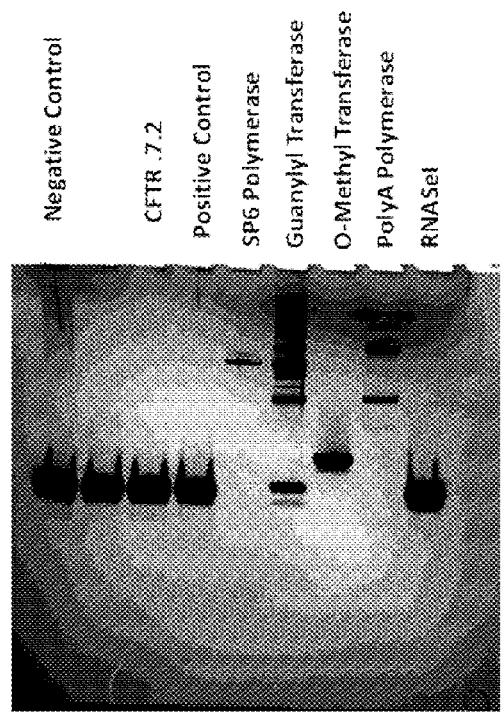

Residual proteins were visualized by gel electrophoresis using SilverQuest™ silver stain as described above in Example 1, and results are shown in FIG. 9A and FIG. 9B. See FIG. 9A and FIG. 9B. As shown in these two figures, the exemplified method resulted in the final obtained C/T mRNA comprising fewer enzyme impurities (FIG. 9B, lane 3).

Example 8: Purification of 10 Grams CFTR mRNA

Cystic Fibrosis Transmembrane Receptor (CFTR) mRNA was prepared according to SP6 RNA polymerase IVT described above.

CFTR mRNA was purified using a horizontal centrifuge. The quenched reaction was QS to eight liters with RNase-free $H_2O$. The reaction mixture was added to 4.6 L of GSCN buffer and mixed for 10 min. 3.4 L of 100% EtOH was then added and mixed for 5 min. (3.3 L of 100% EtOH (see above) then loaded (2.0 L/min) onto a vertical filtering centrifuge (1 µm Filter Paper, 1 µm SLW Filter Cloth) through the sample feed port with centrifuge set to 3000 RPM (1740 G). The mRNA precipitate collected on the centrifuge filter was washed with ten liters of GSCN wash solution (load at 2.0 L/min) through the sample feed port with centrifuge running at 3000 RPM. The mRNA precipitate was then washed with twenty liters of 80% EtOH wash through the sample feed port with centrifuge remaining at 3000 RPM. The mRNA precipitate was dried for fifteen minutes while spinning at 3000 RPM with all ports open to ambient conditions. The dried mRNA precipitate was suspended in water (2×5 L) and pooled to yield 8.3 g of mRNA (83% recovery).

The obtained mRNA was then also purified using tangential flow filtration (TFF). A solution (0.909 mg/L) of the purified mRNA described above was prepared by diluting 8.3 g of the purified mRNA in 9.15 L of RNase-free $H_2O$. The solution was concentrated to 2 L using a TFF column with an H₂O bottom permeate flush. QS to 10 L and repeated concentration for a total of three times. Elutions from the TFF column were collected by clamping the top permeate, stopping the KMPi pump and stopping the bottom permeate pump before collecting the concentrated sample vis the T connection. The weight and concentration of each elution was determined and the yield was calculated. The results are summarized in Table 2 below:

TABLE 2

Dialysis Elution Summary

| Elution | Vol (L) | Conc (g/L) | Yield (g) |
|---|---|---|---|
| E1 | 2.25 | 2.98 | 6.7 |
| E2 | 0.99 | 1.42 | 1.4 |
| E3 | 0.69 | 1.39 | 0.9 |
| Total Yield | | | 9.0 grams (90%) |

CFTR mRNA also can be modified with a cap and tail (C/T) reaction. 9 g of CFTR mRNA obtained following IVT dialysis was diluted to 2 g/L. For the cap reaction, mRNA was treated with 153 mg of GauT, 113 mg 2'OM, 1.44 MU of RNAse Inh; and for the tail reaction, mRNA was treated with 261 mg polyadenylate polymerase (PAP). The reaction had a final volume of 7.2 L, with the cap reaction stirred at 37° C. for 90 minutes, and the tail reaction stirred at 25° C. for 30 minutes.

An initial purification using a horizontal centrifuge (H300P) was then performed. The cap and tail reaction mixture (7.2 L) was treated with 17 L of GSCN buffer and 12.6 L of ethanol. The mixture was then filtered using H300P (1 μM filter paper, 1 μM single layer weave (SLW) filter cloth), with a load rate of 2.0 L/min and with the centrifuge having a rotational speed of 3000 RPM (1740 G). The precipitate was washed with 25 L of an aqueous solution that is 80% ethanol (load rate of 2.0 L/min and rotational speed of 3000 RPM). The precipitate was then dried for 10 minutes in the centrifuge (rotational speed of 3000 RPM). Water was then recirculated in order to suspend mRNA from the filter cloth (two elutions of 3.5 L water each). The first elution (E1) was of a duration of 15 minutes, and the second elution (E2) was of a duration of one hour. The two elutes were pooled to yield 7.6 g mRNA (76% total yield/recovery).

A second purification of the obtained mRNA was performed. The obtained mRNA was treated with 17 L of GSCN buffer and 12.6 L of ethanol. The mixture was then filtered using H300P (1 μM filter paper, 1 μM double layer weave (DLW) filter cloth), with a load rate of 2.0 L/min and with the centrifuge having a rotational speed of 3000 RPM (1740 G). The filtrate was then reloaded using these same conditions and washed with 10 L of a GSCN wash buffer (load rate of 2.0 L/min and rotational speed of 3000 RPM). The precipitate was then washed with 25 L of an aqueous solution that is 80% ethanol (load rate of 2.0 L/min and rotational speed of 3000 RPM). The precipitate was then dried for 10 minutes in the centrifuge (rotational speed of 3000 RPM). Water was then recirculated in order to suspend mRNA from the filter cloth (two elutions of 3.5 L water each). The first elution (E1) was of a duration of 15 minutes, and the second elution (E2) was of a duration of one hour. The two elutes were pooled to yield 6.8 g mRNA (68% total yield/recovery).

The obtained mRNA was then also purified using tangential flow filtration (TFF). 6.5 L of material comprising the 6.8 g of the obtained mRNA (concentration ~1.044 mg/mL) was concentration to 2 L following TFF column with H₂O bottom permeate flush (K04-E100-05-N; 2.0 L/min flow rate). QS to 10 L, including addition of 10 mM sodium citrate, and the solution was re-concentrated. Dilution and concentration was then done for a total of six times, although the sodium citrate was added only to the first load. Elutions were collected by clamping the top permeate, stopping the KMPi pump and stopping the bottom permeate pump before collecting concentrated sample via the T connection. Each elution was weighed to determine volume, and specifications were determined for each elution in order to determine concentration and to calculate yield. The process was repeated as necessary in order to maximize recovery of mRNA, and Table 3 provides a summary of the dialysis elutions. A total yield of 7.6 g mRNA (76% yield) was obtained.

TABLE 3

Dialysis Elution Summary

| Elution | Vol (L) | Conc (g/L) | Yield (g) |
|---|---|---|---|
| E1 | 1.78 | 2.70 | 4.81 |
| E2 | 1.20 | 1.25 | 1.49 |
| E3 | 1.00 | 0.68 | 0.68 |
| E4 | 0.90 | 0.66 | 0.59 |
| Total Yield | | | 7.6 (76%) |

A final dialysis dilution and fill/finish was then performed. 7.2 g mRNA (4.82 L; concentration=1.46 mg/mL) was then diluted to 7.0 L (concentration=1.06 mg/mL), and CFTR mRNA (CFTR.10.1) was filtered through a 0.22 μM sterile filtration cartridge into storage bottles.

Figure 10:
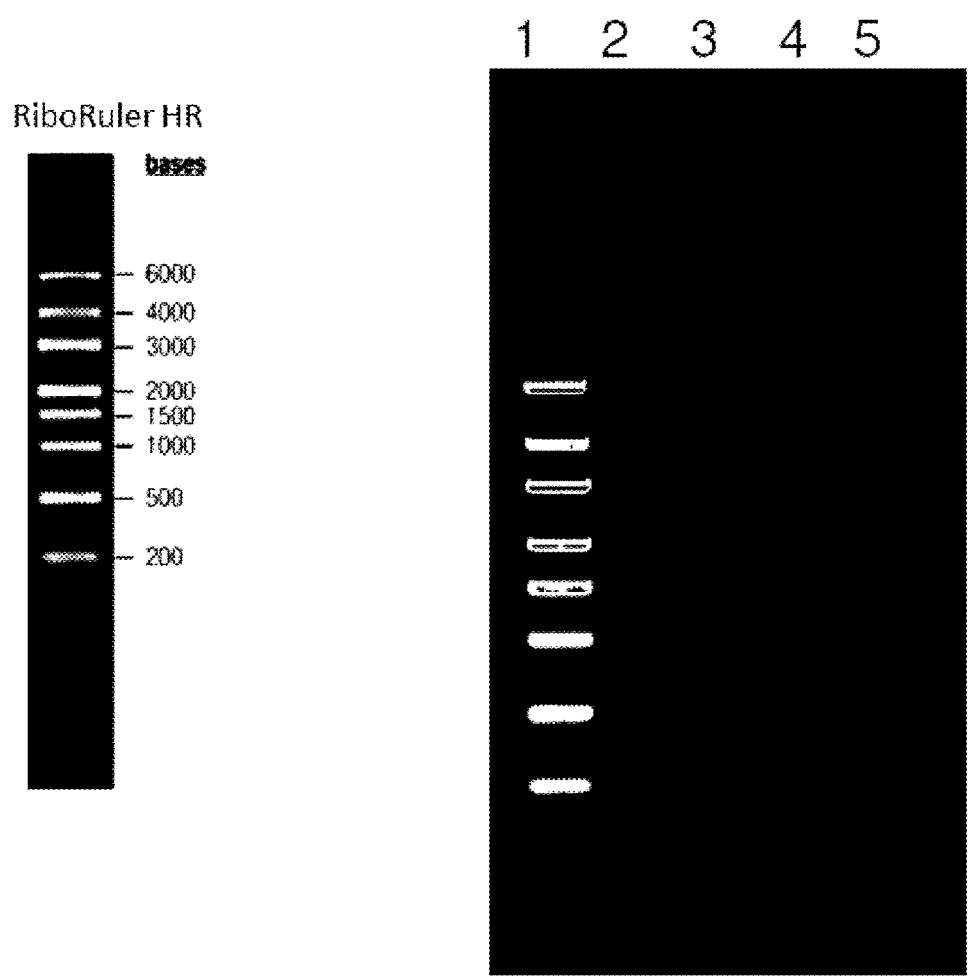
FIG. 10 shows an agarose gel comparing different lots of CFTR mRNA, including mRNA purified according to methods described herein. The gel lane assignments include: Lane 1, pertaining to the Ribo Rule HR Molecular weight marker; Lane 3, pertaining to CFTR.10.1 mRNA prepared according to Example 8; Lane 4, pertaining to CFTR.6.2 mRNA prepared according to Example 6; and Lane 5, pertaining to a control batch of CFTR mRNA purified using TFF.

FIG. 10 shows an agarose gel comparing different lots of CFTR mRNA purified according to methods described herein. Each lane was loaded at 0.5 μg per well. The gel lane assignments include: Lane 1, pertaining to the Ribo Rule HR Molecular weight marker; Lane 3, pertaining to CFTR.10.1 mRNA prepared according to Example 8; Lane 4, pertaining to CFTR.6.2 mRNA prepared according to Example 6; and Lane 5, pertaining to a control batch of CFTR mRNA purified using TFF.

The invention claimed is:

1. A method for large-scale purification of mRNA, comprising steps of:
   providing a suspension comprising at least about 10 grams of precipitated mRNA manufactured by in vitro synthesis; and
   centrifuging the suspension at a speed of about 1000 to 5000 RPM in a centrifuge comprising a porous substrate such that the precipitated mRNA is captured on the porous substrate and contaminants are removed from the precipitated mRNA to provide a purified mRNA,
   wherein the purified mRNA yield is at least about 80% and is substantially free of one or more enzyme reagents used in in vitro synthesis.

2. The method of claim 1, further comprising a step of first producing the suspension of precipitated mRNA by providing a solution comprising mRNA and adding to the solution one or more agents that promote precipitation of mRNA.

3. The method of claim 1, wherein the suspension comprising the precipitated mRNA comprises at least one filtration aid that is a dispersant.

4. The method of claim 1, further comprising adding one or more agents to the suspension that denature proteins and/or keep proteins soluble in an aqueous medium.

5. The method of claim 1, further comprising a step of washing the purified mRNA composition with a solvent.

6. The method of claim 1, further comprising a step of drying the purified mRNA.

7. The method of claim 6, wherein the dried purified mRNA is collected and stored at a temperature of or below about 0° C. for a time period of at least about one week to about two years, and wherein the dried purified mRNA is stored as a solid.

8. The method of claim 7, wherein the dried purified mRNA has substantially the same integrity as prior to storage.

9. The method of claim 1, wherein the purified mRNA is substantially free of prematurely aborted RNA sequences, DNA templates, and enzyme reagents used in in vitro synthesis.

10. The method of claim 9, wherein the enzyme reagents used in in vitro synthesis comprise T7 RNA polymerase, SP6 RNA polymerase, DNAse I, pyrophosphatase, and/or RNAse inhibitor.

11. The method of claim 1, wherein the mRNA encodes cystic fibrosis transmembrane receptor (CFTR).

12. The method of claim 1, wherein the mRNA encodes ornithine transcarbamylase (OTC).

13. The method of claim 1, wherein the method comprises purifying at least about 100 grams mRNA.

14. The method of claim 13, wherein the method comprises purifying at least about 1 kilogram mRNA.

15. The method of claim 14, wherein the method comprises purifying at least about 10 kilogram mRNA.

16. The method of claim 1, wherein the one or more enzyme reagents used in in vitro synthesis is selected from the group consisting of T7 RNA polymerase, SP6 RNA polymerase, DNAse I, pyrophosphatase, and RNAse inhibitor.

* * * * *